US006638475B1

(12) United States Patent
Lagunas-Solar et al.

(10) Patent No.: US 6,638,475 B1
(45) Date of Patent: Oct. 28, 2003

(54) METHOD FOR INHIBITING PATHOGENIC AND SPOILAGE ACTIVITY IN PRODUCTS

(75) Inventors: Manuel C. Lagunas-Solar, Davis, CA (US); Nolan X. Zeng, Sacramento, CA (US); Timothy K. Essert, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 10 days.

(21) Appl. No.: 09/709,757

(22) Filed: Nov. 8, 2000

(51) Int. Cl.[7] ................................................. B01J 19/08
(52) U.S. Cl. ........................................ 422/22; 204/164
(58) Field of Search ............................... 422/186.03, 22, 422/24; 204/164

(56) References Cited

U.S. PATENT DOCUMENTS

| | | |
|---|---|---|
| 1,863,222 A | 6/1932 | Hoermann |
| 1,945,867 A | 2/1934 | Rawls |
| 1,959,390 A | 5/1934 | Smith |
| 2,193,622 A | 3/1940 | Coulter |
| 2,223,813 A | 12/1940 | Brown |
| 2,485,660 A | 10/1949 | Robertson |
| 2,576,862 A | 11/1951 | Smith et al. |
| 3,272,636 A | 9/1966 | Fehr et al. |
| 3,945,170 A | 3/1976 | Brown |
| 4,457,221 A | 7/1984 | Geren |
| 4,522,834 A | 6/1985 | Miyahara |
| 4,524,079 A | 6/1985 | Hofmann |
| 4,624,854 A | 11/1986 | Naumann et al. |
| 4,714,911 A | 12/1987 | Di Mino et al. |
| 4,775,769 A | 10/1988 | Jones |
| 4,808,783 A | 2/1989 | Stenstrom |
| 4,839,142 A | 6/1989 | Charm |
| 4,875,407 A | 10/1989 | Inagaki |

(List continued on next page.)

FOREIGN PATENT DOCUMENTS

| | | |
|---|---|---|
| JP | S50-39126 | 12/1974 |
| JP | S55-15194 | 4/1980 |
| JP | S56-29499 | 7/1981 |
| JP | S56-169550 | 12/1981 |
| JP | S57-56854 | 12/1982 |
| JP | S60-10702 | 3/1985 |
| JP | S60-58669 | 12/1985 |
| JP | S62-163679 | 7/1987 |
| JP | H01-31871 | 6/1989 |
| JP | H02-203773 | 8/1990 |
| JP | H05-24794 | 4/1993 |
| JP | H05-73383 | 10/1993 |
| JP | H06-73432 | 9/1994 |
| JP | H07-47107 | 2/1995 |
| WO | WO 95/24818 | 9/1995 |
| WO | WO 99/13688 | 3/1999 |

OTHER PUBLICATIONS

V. Orsat et al., "Radio–Frequency Treatment for Ready–to–Eat Fresh Carrots," Department of Agricultural & Biosystems Engineering, MacDonald Campus of McGill University, Quebec, Canada & Biotechnology Research Institute, Montreal, Quebec, CAnada (May 22, 2001).

J.N. Ikediala et al., "Quarantine Treatment of Fruits Using Radio Frequency Energy and an Ionic–Water–Immersion Technique," Paper No. 006101, 2000 ASEA Annual International Meeting, Milwaukee, WI(Jul. 9–12, 2000).

*Primary Examiner*—Kishor Mayekar
(74) *Attorney, Agent, or Firm*—John P. O'Banion

(57) ABSTRACT

A method and a system for the application of radio frequency energy to a host material in order to inhibit the presence of pathogenic or spoilage organisms, and the host material thereby treated. In general terms, a radio frequency field is introduced to a host material, where the radio frequency field is configured to resonantly introduce thermal energy to the host material at a frequency, where the thermal energy is sufficient to cause irreversible changes in infective organisms, and where the radio frequency field is configured at a power level such that the thermal energy causes only reversible changes in the host material.

45 Claims, 20 Drawing Sheets

U.S. PATENT DOCUMENTS

| | | |
|---|---|---|
| 4,974,503 A | 12/1990 | Koch |
| 4,975,246 A | 12/1990 | Charm |
| 4,980,530 A | 12/1990 | Butot |
| 5,077,522 A | 12/1991 | Lahitte et al. |
| 5,098,665 A | 3/1992 | Katschnig et al. |
| 5,140,987 A | 8/1992 | Schuger et al. |
| 5,266,766 A | 11/1993 | Hecox |
| 5,288,471 A * | 2/1994 | Corner ................ 422/22 |
| 5,326,530 A | 7/1994 | Bridges |
| 5,339,564 A | 8/1994 | Wilson et al. |
| 5,364,645 A | 11/1994 | Lagunas-Solar et al. |
| 5,405,631 A | 4/1995 | Rosenthal |
| 5,440,104 A | 8/1995 | Koch et al. |
| 5,487,873 A | 1/1996 | Bridges et al. |
| 5,607,711 A | 3/1997 | Lagunas-Solar |
| 5,641,423 A | 6/1997 | Bridges et al. |
| 5,824,605 A | 10/1998 | Chen et al. |
| 5,833,922 A | 11/1998 | Held et al. |
| 5,834,746 A | 11/1998 | Pedersen et al. |
| 5,877,395 A | 3/1999 | Emery |
| 5,896,696 A | 4/1999 | Stokes et al. |
| 5,954,762 A | 9/1999 | Di Mino et al. |
| 5,962,054 A | 10/1999 | Kozempel et al. |
| 5,976,592 A | 11/1999 | Polato |
| 5,977,532 A | 11/1999 | Ekemar et al. |
| 5,980,824 A | 11/1999 | Kartchner |
| 6,093,432 A | 7/2000 | Mittal et al. |
| 6,246,040 B1 * | 6/2001 | Gunn ................ 219/771 |
| 6,303,166 B1 * | 10/2001 | Kolbe et al. ............ 219/771 |

* cited by examiner

METHOD FOR INHIBITING PATHOGENIC AND SPOILAGE ACTIVITY IN PRODUCTS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to a method and a system for the application of radio frequency energy to products, such as agricultural commodities or valuable artifacts, in order to inhibit the presence of pests, bacteria, and other pathogenic or spoilage organisms. The present invention is also directed to the products treated with such radio frequency energy.

2. Description of the Background Art

Major human safety concerns exists today on the potential contamination food commodities with pathogenic bacteria such as *Escherichia coli* O157:H7, Salmonella sp., Listeria, and especially Campylobacter (see, for example, J. L. Welbourn: "Inside Microbiology", in Food Testing & Analysis, pp. 20–22 Vol., 4 (3) June/July 1998). Each of these pathogenic bacteria has recently been identified as disease causing agents from the consumption of many common food commodities. Estimated food borne illness outbreaks and deaths annually in the United States affect 12 million and 4,000 individuals, respectively. Agricultural commodities such as grains, seeds, and spices may also be affected by fungal and/or bacterial contaminants. In addition, the keeping quality of agricultural commodities may also be affected by enzyme activity. Further still, microbial activity may generate a variety of toxins (i.e. Aflatoxin from *Aspergillius flavus* in grains).

Accordingly, it is desirable to inhibit the presence of disease-carrying organisms within food and agricultural commodities. Two manners of accomplishing this include slowing down the development of spoilage organisms (biostatic effects) or using thermal energy to cause a lethal effect on the organism (biocidal effect).

A. Thermal Sensitivity Trends

One manner of inhibiting the presence of such infective organisms, such as pathogens and insect/arachnid-type contaminants, is with thermal energy. The use of thermal energy to attack microorganisms within a host material is based on the fact that microorganisms will possess a greater sensitivity and vulnerability to thermal energy than the host materials. (i.e. agricultural commodities and other materials). This greater sensitivity is due to the greater complexity in the organism's biological structure, as well as due to the existence of complex functional processes that are needed to sustain living organisms such as respiration, energy production, and cell division.

By way of illustration only, FIG. 1 depicts the relative sensitivities of host materials and infective organisms to thermal energy. Boundary 130 indicates the temperature at which irreversible changes occur in the host material. In FIG. 1, different classes of host material are allocated relatively different boundaries. Accordingly, fresh fruits are in region 131, plants in region 132, seeds in region 133, grains in region 134, and soils in region 135. FIG. 1 indicates that host material high boundary 130 is greatest (in a relative sense) in soils, and is lowest (in a relative sense) in fresh fruits. As used herein, "irreversible" changes in the host material include (i) changes that affect the host material's inherent metabolic and/or physiological attributes affecting the host material sensory and storage properties, or (ii) changes that affect the host material's inherent chemical and molecular structure affecting the host material's sensory and storage properties. For example, a host material that possesses some inherent metabolic activity is a green tomato following its harvest. A green tomato that is harvested and in conventional storage will continue to undergo metabolic changes associated with a color change (from green to red) and changes in chemistry that account for the taste of a ripe tomato. Accordingly, an irreversible change is a change that alters the host material's inherent metabolic and/or physiologic attributes. For example, pickling vegetables or canning fruits alters the vegetable's or fruit's inherent metabolic activity and would, thus, be considered an irreversible change.

Alternatively, an example of a host material with a specific chemical or molecular structure that accounts for the host material's sensory or storage properties is an artifact such as an antique book or an art object. In an antique book, the chemical or molecular structure of the ink on the page, or the molecular structure of the page itself accounts for the sensory properties associated with the book (i.e., color) as well as its potential value. Such molecular structure or chemical structure may be altered over a long period of time by the presence of spoilage organisms. Furthermore, the host material itself may be consumed by insects or mites. Accordingly, an irreversible change in such a host material is a change that alters the chemical or molecular structure of the host material so as to alter its sensory properties such as color, or its storage properties.

Further still, and in fresh fruits, inherent physiological properties include appearance, structure, and taste. Below boundary 130 (and above boundary 120) in FIG. 1, only "reversible" changes occur in the host material. Examples of reversible changes include such processes as small changes in temperature, where the temperature may cycle up and then down with no net change in the host material's inherent metabolic and/or physiological attributes, or in the host material's chemical or molecular structure as described above. Boundary 110 indicates the point above which irreversible changes occur in insects and arachnids. As used herein, "irreversible" changes in infective organisms include changes that affect the organism's ability to reproduce or the ability to survive. By way of illustration, below boundary 110 (and above boundary 100) reversible changes occur in insects and arachnids. Further still, boundary 120 indicates the region above which irreversible changes occur in microbes. Again, by way of illustration, below boundary 120 (and above boundary 110) reversible changes occur in microbes.

As stated above, thermal sensitivity in living matter is in direct proportion to biological complexity. Therefore, a high degree of biological complexity results in a high sensitivity to thermal energy. In FIG. 1, it is noted that insects and arachnids are the most sensitive, while soils are the least sensitive. The microbes depicted in FIG. 1 include fungi and yeasts, bacteria, viruses, and protozoa. Furthermore, and with respect to insects and arachnids in all life cycles, an induced thermal level of 40–60° C. results in instant or delayed mortality or disruption of reproductive activity. When microorganisms are subjected to thermal energy only slightly above their maximum growth temperatures, an irreversible change, such as the reduction of viable cells or spores, generally follows. It is believed that this behavior is due to the denaturation of proteins, enzymes, or genes essential to reproduction. This is generally described in "Physical Principles of Food Preservation," part II, ed. Owen R. Fennema, Marcel Dekker Inc., 1975. Further still, although a valuable artifact such as an antique book or an art object may not have any "biological complexity" as described above, the host material may be nevertheless highly sensitive to environmental factors, such as temperature, that may alter the host materials inherent chemical or molecular structure.

Accordingly, the application of thermal energy to a living-organism/host-material system, such as an infected food product or an infected artifact, can be utilized to target enzyme activity primarily and therefore the functional capabilities of living organisms. Enzyme inactivation is a critical goal in rendering a variety of products free of living contaminants such as insects, arachnids (i.e. mites), and microbes. The application of thermal energy to living organisms also imposes sub-lethal stress, which may lead to delayed mortality, and tissue damage due to the expansion of liquids.

B. Non-Uniformity of Conventional Thermal Energy Production

Despite its usefulness in inhibiting the presence of pathogenic organisms, thermal energy is usually introduced on a limited basis to host materials such as fresh food or other artifact due to the irreversible changes introduced to the host material's metabolic, physiological, chemical, molecular, sensory, or storage properties. One reason for this is that thermal energy is usually introduced through conduction, convection, and conventional microwave radiation. With the qualified exception of microwave radiation discussed below, an aspect of these conventional methods of introducing thermal energy is that one region of the host material, such as the surface, is initially exposed to more thermal energy than a neighboring region. This thermal energy, then, dissipates to the neighboring region through the process of conduction or convection. In all cases where this type of heat processing is used, it is necessary to apply a greater amount of thermal energy to one region in order to allow for heat transfer to be effective in distributing a sufficient amount of thermal energy to reach and control contaminating organisms over the entire product volume. As a result, heat applied to the host material through the selected region is often excessive and causes an irreversible change to that region, resulting in unacceptable damage.

Commercial applications for disinfection and/or disinfestation that attempt uniform thermal energy distribution are typically limited. An example of a technique used for a food product such as a mango is the hot water dip, which has varying results for the reasons discussed above.

C. Basic Concepts and Operation of Radio Frequency Radiation

Radio frequency (RF) radiation refers to electromagnetic radiation in the frequency range from approximately 3 kilohertz to 300 gigahertz. The ability of host material to absorb RF radiation generally varies as a function of frequency. FIG. 2 depicts an exemplary plot of absorption curve 200 of a host material versus frequency across a subset, for example, of the frequencies associated with RF radiation. A local maximum 210 at frequency $f_0$ in the absorption curve identifies a frequency, conventionally understood as a "resonant" frequency, associated with a given host material. One skilled in the art should appreciate that the resonant frequency $f_0$ is generally dependent upon the host material, including its geometry and dielectric properties. In resonance mode, RF energy is maximally transferred to the host material, providing a somewhat efficient transfer of energy. It can introduce thermal energy to a host material homogeneously and at controlled levels throughout the mass of the commodity.

Transferring thermal energy through RF radiation to a host material is different from processes that are based on conduction, convection, and conventional microwave-radiation. The dominant difference is due to the fact that RF processing can introduce thermal energy uniformly throughout the host material. In the conventional methods itemized above (with the exception of microwave radiation, discussed below), thermal energy is introduced to one region, for example, the surface, and is then transferred to the remaining regions through conduction or convection. Energy losses from the host material's surface may be significant, requiring further thermal energy input in order to achieve the intended biocidal effect.

Unlike conduction and convection, however, the interaction between RF radiation and a host material and conventional microwave radiation and a host material is analogous. RF radiation, however, encompasses frequencies lower than the frequency of a conventional microwave oven, which is approximately 2,450 MHz. Because of this, RF radiation is able to generate thermal energy more homogeneously, deeper within a host material, and with less possibility of irreversible change to the host material.

Dipolar molecules within host material absorb both RF radiation and conventional microwaves. The differences between the effects that each have on the host material is due to their difference in frequency and wavelength. Conventional microwaves in a microwave oven have a frequency of approximately 2,450 MHz, and a wavelength of approximately 12.2 cm (approximately 4.8 inches). The separation between anti-nodes, therefore, is approximately one-half of a wavelength, or 6.1 cm (2.4 inches). Accordingly, and in a macroscopic object, the portions of the microwave radiation field that may not be imparting any energy to the macroscopic object are separated by approximately 6.1 cm or 2.4 inches. This accounts for the uneven heating ordinarily present in microwave ovens as well as for the typical practice of moving an item around inside a microwave cavity in order to achieve a semblance of uniform heating.

Alternatively, and considering RF radiation in the range of 100 MHz (approximately an order of magnitude lower in frequency than conventional microwaves), the wavelength of such RF radiation is approximately 300 cm (9.8 feet). Applying the same analysis as above, the separation between anti-nodes in such RF radiation is 150 cm (4.9 feet). Thus, the regions of uneven heating in such a RF radiation field are at most separated by 4.9 feet, which is well beyond the dimensions of a typical food product. Accordingly, RF radiation interacts more uniformly and deeply within a host material than does conventional microwave radiation. Such a general effect is recognized in U.S. Pat. No. 5,977,532, herein incorporated by reference.

The difference in frequency also accounts for the other major difference between RF radiation and microwave radiation: the fact that RF radiation is less likely to cause irreversible change in the host material than conventional microwave radiation. The frequency of microwave radiation is approximately one order of magnitude higher than RF radiation in the 100 MHz range. Accordingly, each photon that is absorbed and is not re-emitted (the primary means of energy absorption by a host material) imparts an order of magnitude more energy to the host material than does a photon of RF radiation in the 100 MHz range. This, of course, is desirable when one wishes to cook a food, since the whole goal of cooking is to introduce an irreversible change to the host material. However, conventional microwaves are undesirable when applied to fresh fruit, for example, and when one wishes no change in the qualities associated with freshness (such as appearance and taste).

This energy difference is also reflected in the formula that describes the absorption of RF radiation of the present invention by a host material. The power generated by RF radiation in a host material can be written:

$$P=55.61\times10^{-14}E^2f\in''$$

Where: P is the power density generated in the host material (in W/cm$^3$); E is the electric field strength (in V/cm); f is the RF frequency (in Hz); and $\in''$ is the dielectric loss factor of the host material (dimensionless). The dielectric loss factor $\in''$ is an intrinsic property of the host material. As stated above, and as is obvious from the above equation, a magnitude drop in frequency corresponds to a magnitude drop in transferred power at the same field strength.

Therefore, for most fresh agricultural commodities, microwave heating is not adequate, as it does not produce homogeneous heating. Microwave heating is also not homogeneous when large volumes of plant tissue are treated due to the rather limited penetration of 2,450 MHz photons. In addition, the high absorption of microwaves in water (a major component of fresh plant tissue) does not allow for low-level thermal treatments in a controllable manner.

D. Conventional RF Systems

The traditional or standard RF system used for RF heating is given in FIG. 3. The product sample 310 is placed inside Transversal Electromagnetic Cell 300 (TEM Cell 300). The RF wave travels across the cavity and interacts with sample 310. The remaining power exits on the opposite end and is measured as output power. The entire system operates in a single-pass transversal mode.

During this standard RF process, the RF input power $P_i$, the reflected power $P_r$, and the output power $P_o$ are measured. The flow of RF power exiting TEM Cell 300 ($P_o$) is terminated in a heat sink cooled by forced air or a circulating coolant. Depending on how well the electromagnetic field interacts with the target, there are at least two possible outcomes.

In the first outcome, if there is no sample 310 in TEM cell 300, if the RF wave does not couple well, or if the RF wave hardly interacts with sample 310, the output power $P_o$ is roughly equal to the input power $P_i$ and the reflected power $P_r$ is roughly equal to zero. In this outcome, the absorbed RF power $P_{ab}$ may be written as:

$$P_{ab}=[P_i-P_r-P_o]=0$$

Thus, there is no energy transferred from the RF wave to the sample, and sample 310 is not actually heated.

In the second outcome, if an appreciable coupling exists between the RF wave and sample 310, an effective energy transfer from the RF wave to sample 310 will take place. In this outcome, the impedance of the RF system changes, the reflection power $P_r$ increases and the output power $P_o$ is reduced. Accordingly, the absorbed RF power $P_{ab}$ may be written as:

$$P_{ab}=[P_i-P_r-P_o]>0$$

In this situation, the sample temperature increases proportionally to the absorbed power $P_{ab}$ and this change may be expressed as:

$$\Delta T=T_{fin}-T_{ini}$$

Where $T_{fin}$ is the final temperature of the sample and $T_{ini}$ is the initial temperature of sample 310. The ratio of the absorbed power to the input power ($P_{ab}/P_i$) is an important parameter that indicates the fraction of input RF power absorbed by sample 310. This absorbed/input power ratio $R_{ab}$ is given by:

$$R_{ab}=P_{ab}/P_i=1-(P_r+P_o)/P_i$$

A high absorbed-power ratio $R_{ab}$ is desirable for best efficiency and lower cost. It also implies that a higher temperature differential ($\Delta T$) can be obtained for sample 310. These latter aspects allow processing with different thermal energy levels within the host material's thermal window.

Experimental data indicates that the use of standard RF processing using the conventional RF system approach shown in FIG. 3 results in a maximum absorbed power ratio $R_{ab}$ of approximately 50–60%. Accordingly, the overall use efficiency and the temperature gradients available are both limited and low. Under the above conditions, commercial, large-scale uses of RF processing may be limited by both economic and practical considerations.

Accordingly, it is desirable to have a system that generates a high absorbed-power ratio $R_{ab}$ for use with RF processing.

E. Comparison With Prior Technology Using Electromagnetic Radiation

Prior technology directed towards the incapacitation of infective organisms have tended to focus on the targeting of the organisms with electromagnetic radiation of power, intensity, and frequency sufficient to inhibit the microorganisms directly (non-thermal effects).

U.S. Pat. No. 4,524,079 to Hoffman et al. (the '079 patent), herein incorporated by reference, teaches the use of an oscillating magnetic field in the frequency range between 5 kilohertz and 500 kilohertz in order to reduce microorganisms. One skilled in the art should appreciate that dynamic magnetic fields will induce electrical currents in tissues proportional to the change in the magnetic field and the conductivity of the tissue. The '079 patent teaches that frequencies above 500 kilohertz are less effective in deactivating microorganisms by magnetic oscillation and will tend to heat the material, which is considered undesirable. The intensity of the applied field is disclosed in the '079 patent as between 2 and 100 Tesla. Fields with intensities above 2 Tesla are generally accepted as having adverse effects on biological tissue. Furthermore, the magnetic field of the earth is at least 4 orders of magnitude smaller (approximately $10^{-4}$ Tesla) than that disclosed in the '079 patent.

U.S. Pat. No. 5,339,564 to Wilson et al. (the '564 patent), herein incorporated by reference, teaches the use of frequency-hopping RF power (147 MHz and 240 MHz are examples of frequencies disclosed). The frequency is chosen to couple only to the natural polarization oscillations of animal mitochondria. The '564 patent teaches that the frequencies do not harm plant cells because of their different structure. In addition, the '564 patent states that dipole oscillations occur between 1 kilohertz and 1 megahertz, whereas the process of coherent excitation occurs at frequencies close to 100 MHz. The disclosed intensity at 147 MHz is 8 watts/m$^2$.

U.S. Pat. No. 3,272,636 to Fehr et al. (the '636 patent), herein incorporated by reference, teaches the use of a frequency range of 20 to 40 MHz, and intensity between 500 and 3000 volts per centimeter r.m.s. Again, the frequency chosen to be lethal to disease bearing microorganisms and destructive to the reproductive ability of organisms that causes food commodities to spoil without causing appreciable heat. The '636 patent teaches that this frequency range does not cause internal heating of the food sufficiently to cook the food or change its flavor. The '636 patent also teaches that lower frequencies could be used in instances where the food product is resistant to penetration by higher frequencies, or if the microorganism is more susceptible to lower frequencies. Furthermore, the '636 patent teaches the use of higher frequencies up to the "dielectric heating range" (1000 MHz) if additional heating or cooking of the food product is not important. As with the other references above, the '636 patent teaches that the microorganisms are inhibited directly by the RF radiation at high power.

U.S. Pat. No. 2,485,660 to Robertson (the '660 patent) discloses the use of plasma frequency emissions in the range of 1 MHz to 1000 MHz, with the preferred frequency being around 30 MHz or above. The frequency and power output are chosen to create an invisible corona discharge, which kills the living organism without appreciable heating of the surrounding media.

Accordingly, there is a need for a commercial process for causing irreversible changes to infective organisms while causing only reversible changes to the host materials such as: fresh fruits and vegetables; meat, poultry, and seafood; grains, seeds and spices; and valuable artifacts. This is due to the fact that fresh fruits, vegetables, and artifacts are normally affected by a heat-sensitive natural flora of spoilage organisms and, sometimes, as with fresh fruits and vegetables, experience an additional contamination with pathogenic organisms (bacteria) due to handling and packaging. No conventional method based upon thermal energy is presently used. The application of RF radiation to grains, seeds, and spices has many objectives, as these host materials may be affected by fungal and/or bacterial contaminants. In all these cases, an RF method is able to provide a decontamination effect improving the general safety of these host materials. Furthermore, an RF method is able to preserve valuable artifacts such as antique books. Further still, thermal inactivation of enzymes promoting biochemical degradation of essential nutrients is a major application of the RF method leading to a better, non-chemical preservation technology for grains.

BRIEF SUMMARY OF THE INVENTION

Accordingly, in a first embodiment of the present invention, a method for treating products includes introducing a radio frequency field determined by parallel-plate electrode geometry to a product containing a host material, where the radio frequency field is configured to resonantly introduce thermal energy to the host material at a frequency, where the thermal energy is sufficient to cause irreversible changes in infective organisms, and where the radio frequency field is configured at a power level such that the thermal energy causes only reversible changes in the host material.

In a second embodiment of the present invention, the system comprises a TEM Cell in which the terminating resistance is eliminated by: matching a product's geometry with the electromagnetic field, forming a harmonic resonator with the commodity, and coupling the electromagnetic field with the product's dielectric loss factor.

A third embodiment of the present invention comprises the host material treated by the method consistent with the first embodiment described above. Another embodiment of the present invention comprises: introducing a radio frequency field to a product comprising a host material where the radio frequency field is configured to be absorbed by the product at a rate less than approximately 500 watts for a time period between approximately 2 hours and 20 hours, and where the radio frequency field is configured to exhibit a frequency between approximately 800 kilohertz and 2 megahertz.

A further embodiment of the present invention comprises the host material treated by the above method.

Further still, another embodiment of the present invention comprises: a TEM Cell in which the terminating resistance is eliminated and the radio frequency radiation is configured to couple with the product such that: the output power and the reflected power are minimized, the radio frequency radiation is absorbed by the product at a rate less than approximately 500 watts for a time period between approximately 2 hours and 20 hours, and the radio frequency radiation is configured to exhibit a frequency between approximately 800 kilohertz and 2 megahertz.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
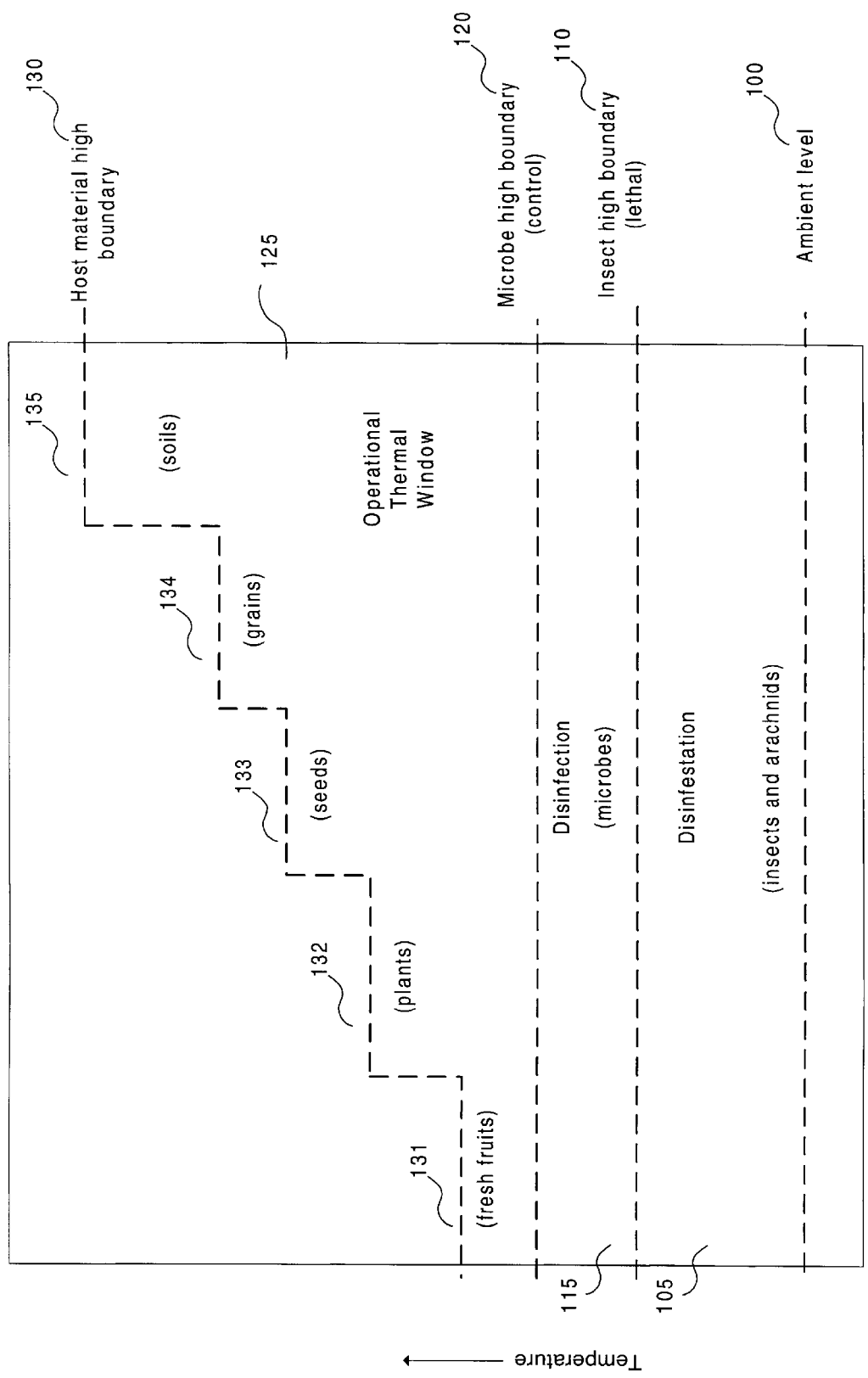
FIG. 1 depicts an exemplary operational thermal window consistent with the present invention.
Figure 2:
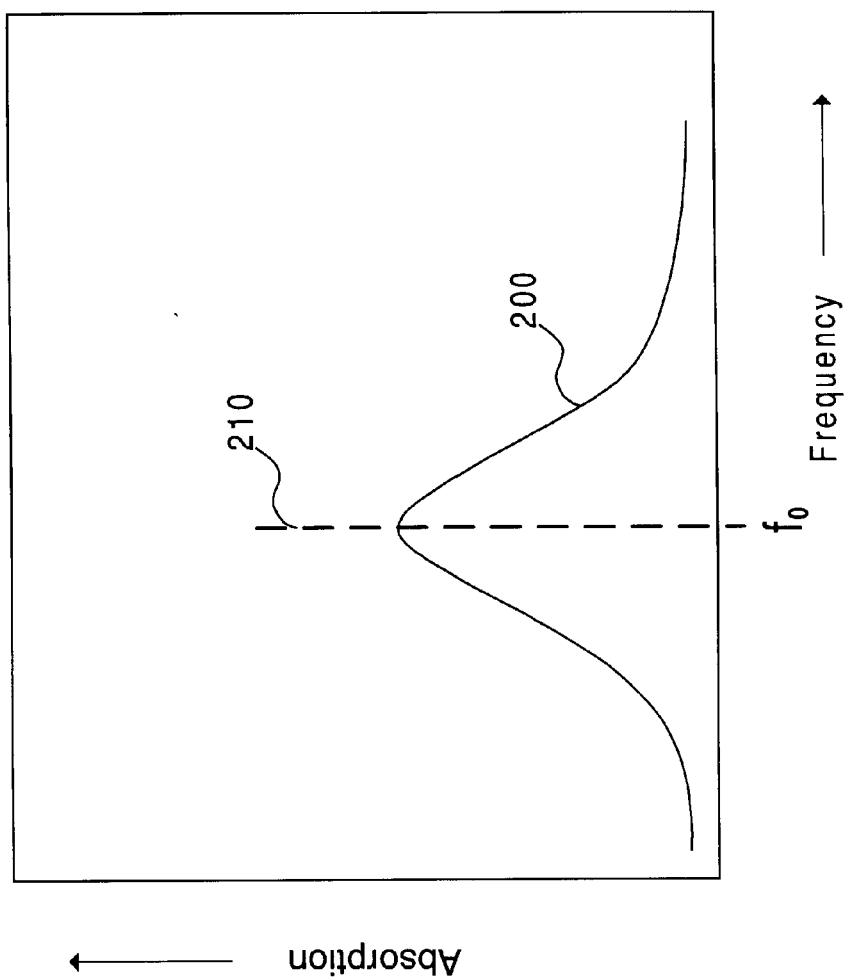
FIG. 2 depicts a plot of absorption versus frequency for a host material in the region of a resonance.

In one embodiment, the RF method consistent with the present invention is based on the use of RF radiation to induce an acceptable or tolerable thermal energy level homogenously within an acceptable or tolerable thermal range ("thermal window") for a host material. Therefore, the RF method allows for the use of a low thermal energy level (temperature) that is sufficiently high to be lethal to many organisms, but that is kept below the level causing unacceptable metabolic, physiological, chemical or molecular changes in the host material.

The method of the present invention is accomplished by placing a product between two parallel plate electrodes ("applicators"). The applicator of the present invention may be designed for a particular type of product and will allow treating the product with its final package (prior to shipment). The design considerations include both geometry of the product as well as the voltage capability of the applicator. Exemplary geometries are itemized below.

As used herein, the term "product" refers to the combination of host material, any potential infective organisms, and various packaging. Packaging may encompass wrapping, lunchboxes (i.e. obentos), or any type of storage or presentation structure.

For the RF method to be efficient in generating heat homogeneously throughout the mass of the host material, the RF frequency used must be highly penetrating and the host material's composition reasonably homogeneous. In order to achieve this condition with host material of different densities and slight different chemical compositions, the range of operating frequencies can be between 0.1 to 1,000 MHz, but preferably in the 30 to 300 MHz range. Furthermore, once the RF applicator for a particular product geometry is defined, the best operating RF frequency can be generated by adjusting the inductance in the RF resonant circuit described below. In this manner, high power conversion (RF power to thermal energy) and high penetration are obtained for specific product to be treated with the RF method.

However, because the RF method being disclosed here is established primarily at a single or at a narrow-band resonance frequency for a particular product, the method is optimized when coupling the RF energy frequency to the dielectric loss factor of the product, which is primarily governed by chemical composition. In this manner, the variables affecting the heat generated within the host material are different from those that affect heat-flow characteristics from its surface. In fact, the many similarities and quality factors normally encountered in commercial fresh produce (including packaging) allows one to establish the best operating conditions (i.e., matching RF frequency, product composition, and geometry) without affecting the overall efficiency of the RF Process.

As stated earlier, a review of the available literature indicates that thermal energy levels of 40–60° C. (or $\Delta T \approx 20$–$40°$ C.) are sufficiently high to induce disinfection and/or a disinfestation level adequate for the majority of host materials needing decontamination. At these temperature levels, and for short times, the sensory, functional, and marketing characteristics of these host materials can be maintained or potential effects can be minimized.

A. High Use/Conversion Efficiency RF Processing

Figure 3:
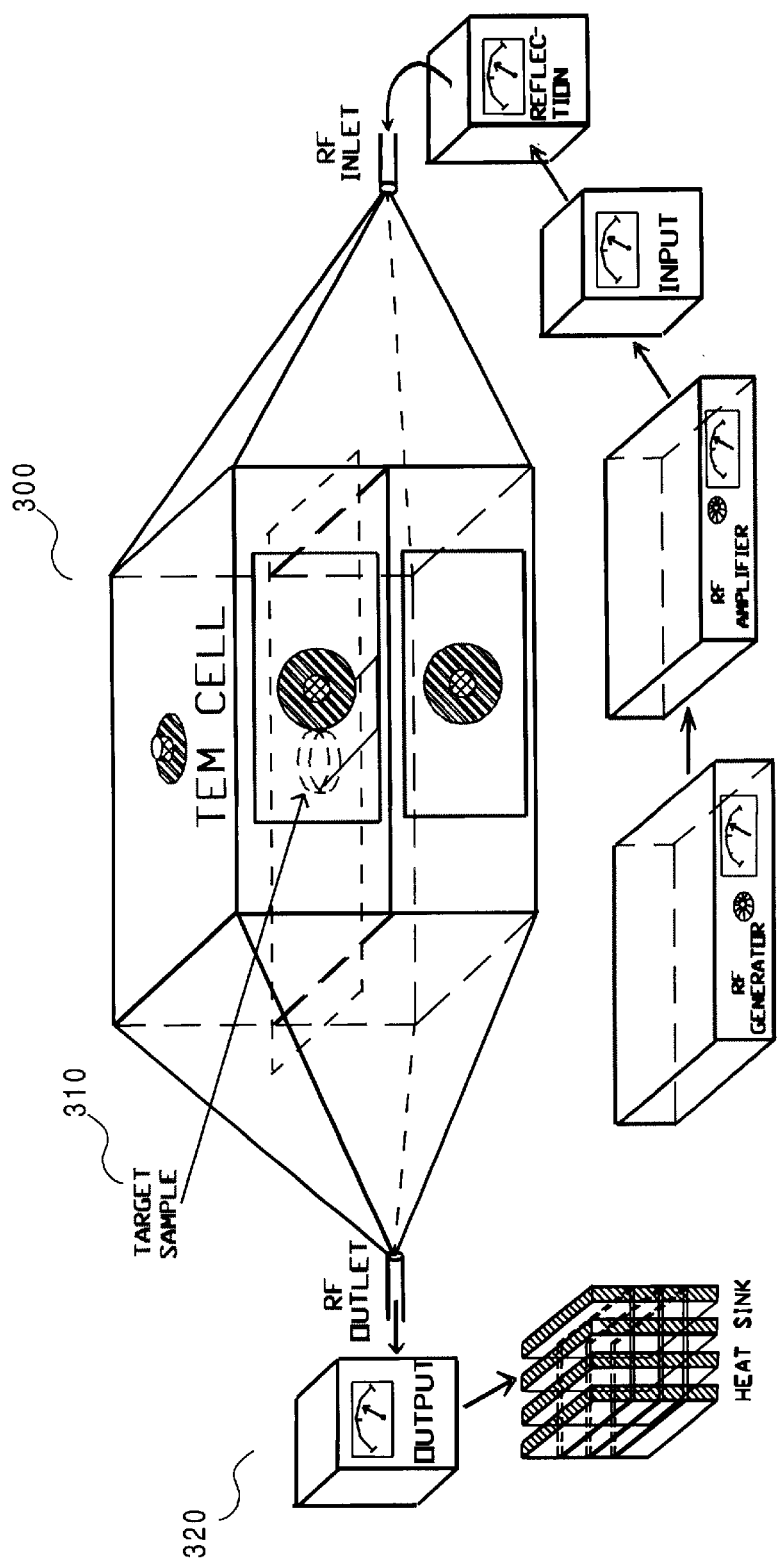
FIG. 3 depicts a TEM Cell of the prior art.
Figure 4:
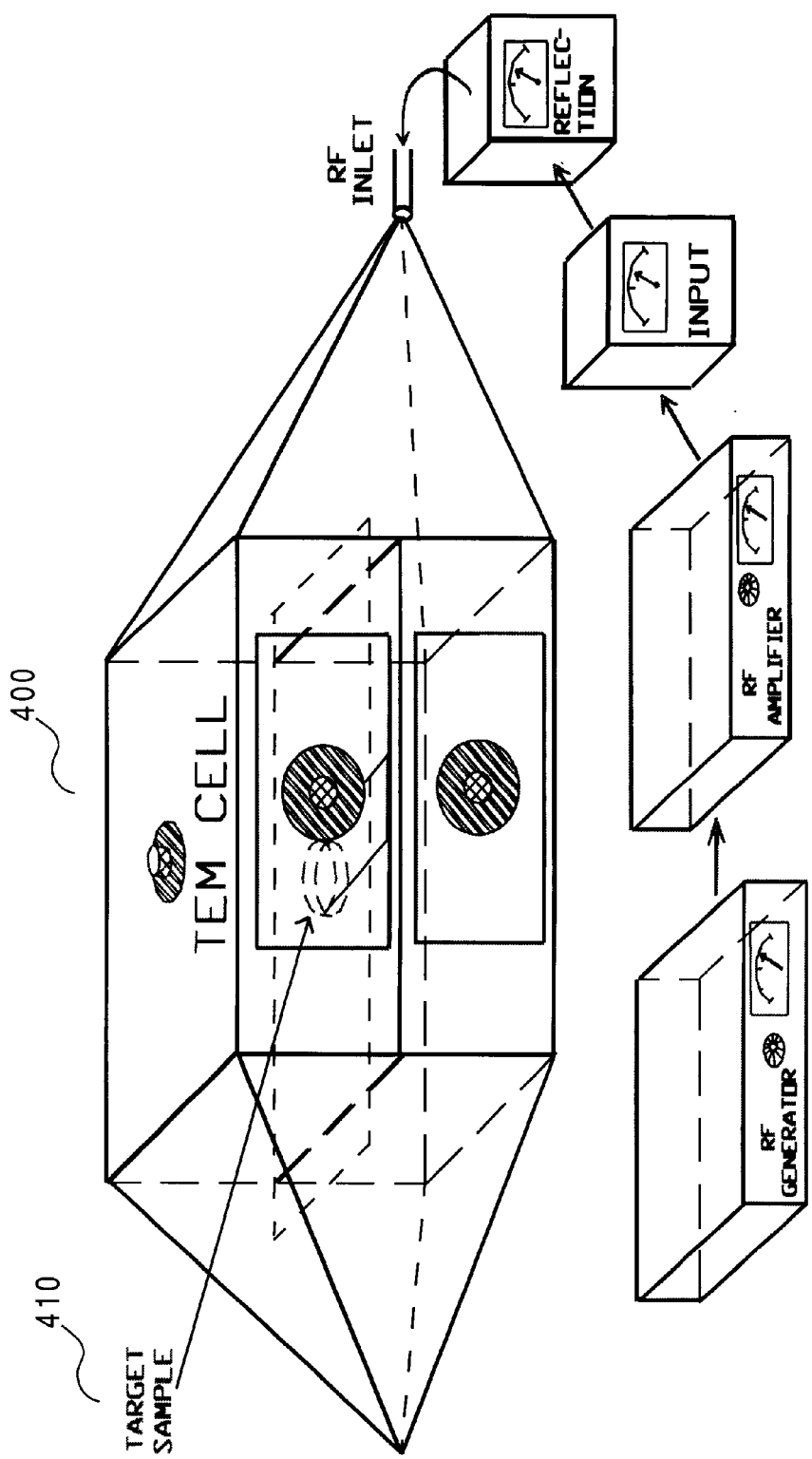
FIG. 4 depicts a TEM Cell consistent with the present invention.

A high use/conversion efficiency (HUCE) RF system consistent with the present invention is depicted in FIG. 4 as TEM Cell 400. In this system, and compared against the prior art system of FIG. 3, the terminating resistance is eliminated. This is achieved by making sample 410 a low-impedance load. Therefore, contrary to conventional approaches, there is no output RF power (i.e. $P_o$=0), and the RF reflected power $P_r$ can be minimized (i.e. $P_r$=0). This results in a significant improvement in power use and power conversion efficiencies.

This is achieved by: matching a specific product's geometry (i.e. host material and its package) with an appropriate electromagnetic field determined by the boundaries set by parallel plate electrodes; increasing the electric field strength by forming a harmonic resonator with the product being the dielectric media; and coupling the electrical field with the product's dielectric loss factor, making the RF process efficient and specific for a product or for groups of similar commodities.

The above effects were achieved by converting the single pass (unidirectional) transversal RF wave conventional system (TEM Cell 300 of FIG. 3) into a product specific resonant cavity that operates more efficiently in converting RF power into thermal energy within the product. With this modification, the absorbed power ratio $R_{ab}$ is given by $$R_{ab} = 1 - P_r/P_i$$

Under these conditions, the absorbed power ratio $R_{ab}$ for the HUCE RF system (TEM Cell 400) is consistently greater than 90%.

Figure 5:
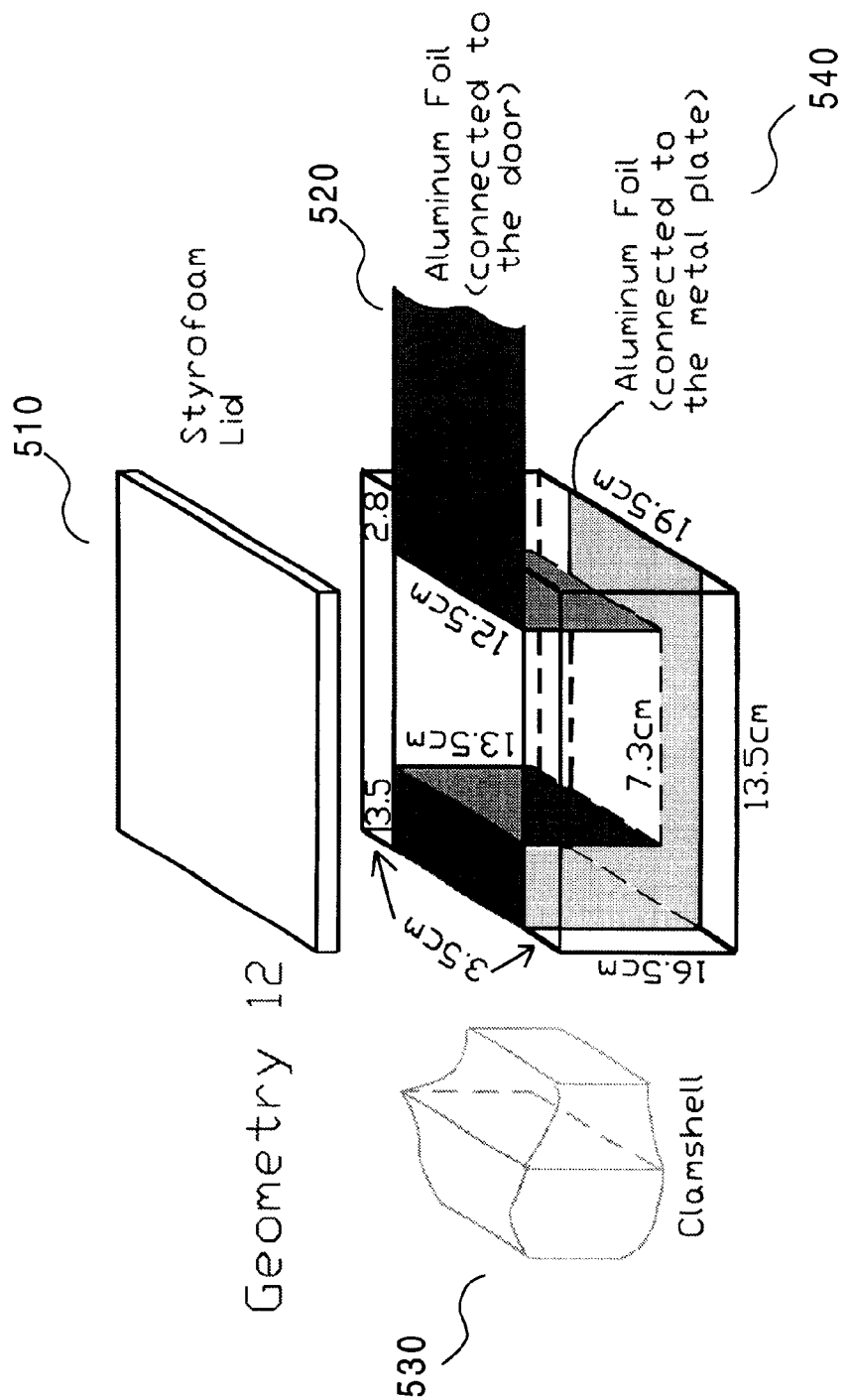
FIG. 5 depicts the dimensions and structure of "geometry-12" as used herein, or the "clamshell" geometry.
Figure 6:
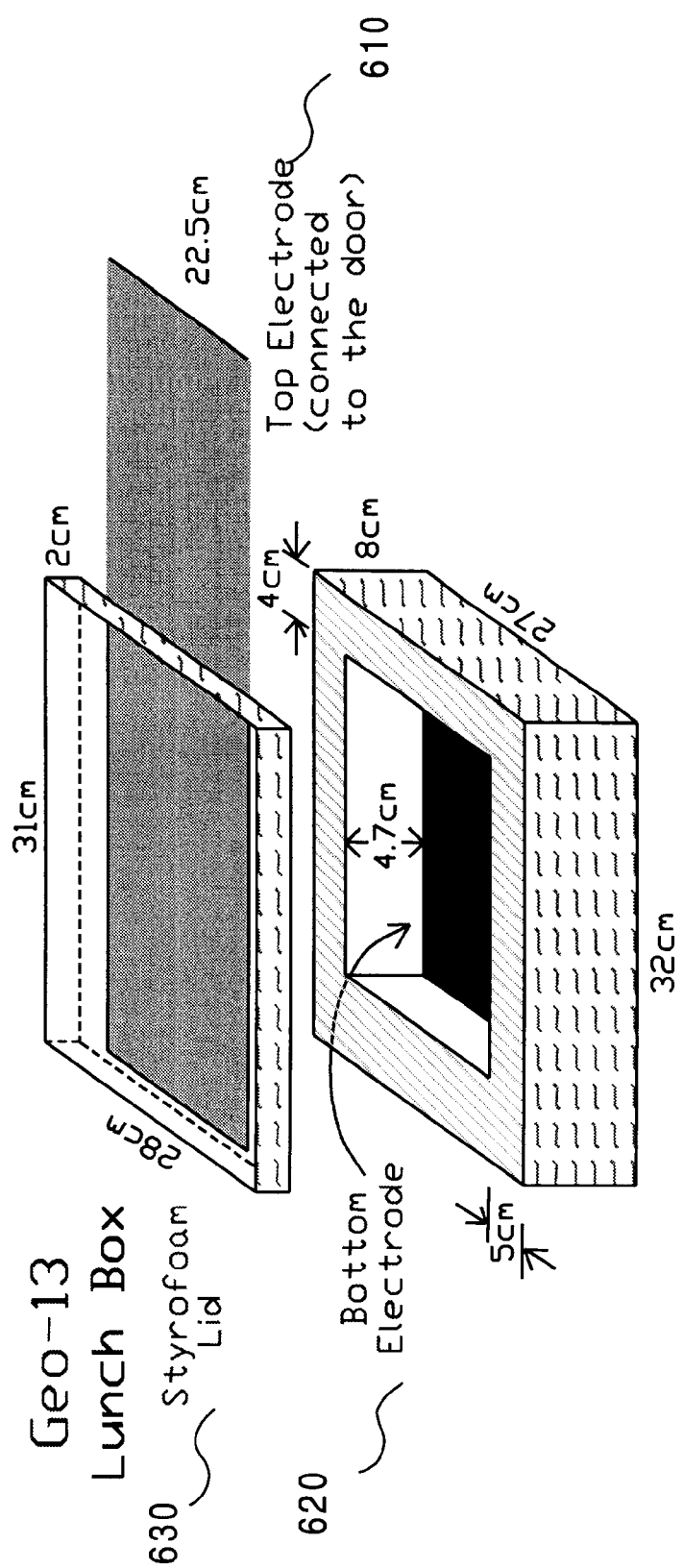
FIG. 6 depicts the dimensions and structure of "geometry-13" as used herein, or the "lunchbox" geometry.

As stated earlier, the applicator of the present invention may be designed for a particular type of product and will allow treating the product with its final package (prior to shipment). Accordingly, one of the design considerations is the geometry of the product. Table 1 below, itemizes exemplary geometries consistent with the present invention. By way of illustration, two specific geometries are further illustrated in FIG. 5 and FIG. 6. FIG. 5 depicts "geometry- 12" as used herein, associated with the "strawberry clamshell" commercial packaging. FIG. 6 depicts "geometry-13" as used herein, associated with the "lunchbox" packaging. In all, Table 1 itemizes twenty-seven geometries consistent with the present invention as well as the associated host material or packaging. In the "comments" column, "$4\pi$ Styrofoam insulation" indicates that the Styrofoam insulation subtends a solid angle of $4\pi$ steradians.

Again, as stated earlier, the absorbed power ratio $R_{ab}$ for the HUCE RF system (TEM Cell 400) is consistently greater than 90%. This is demonstrated by comparing thermal absorbed power between the HUCE RF system (TEM Cell 400) and the conventional RF Processing TEM Cell 300, using the same spectrum of food and non-food commodities.

Figure 7:
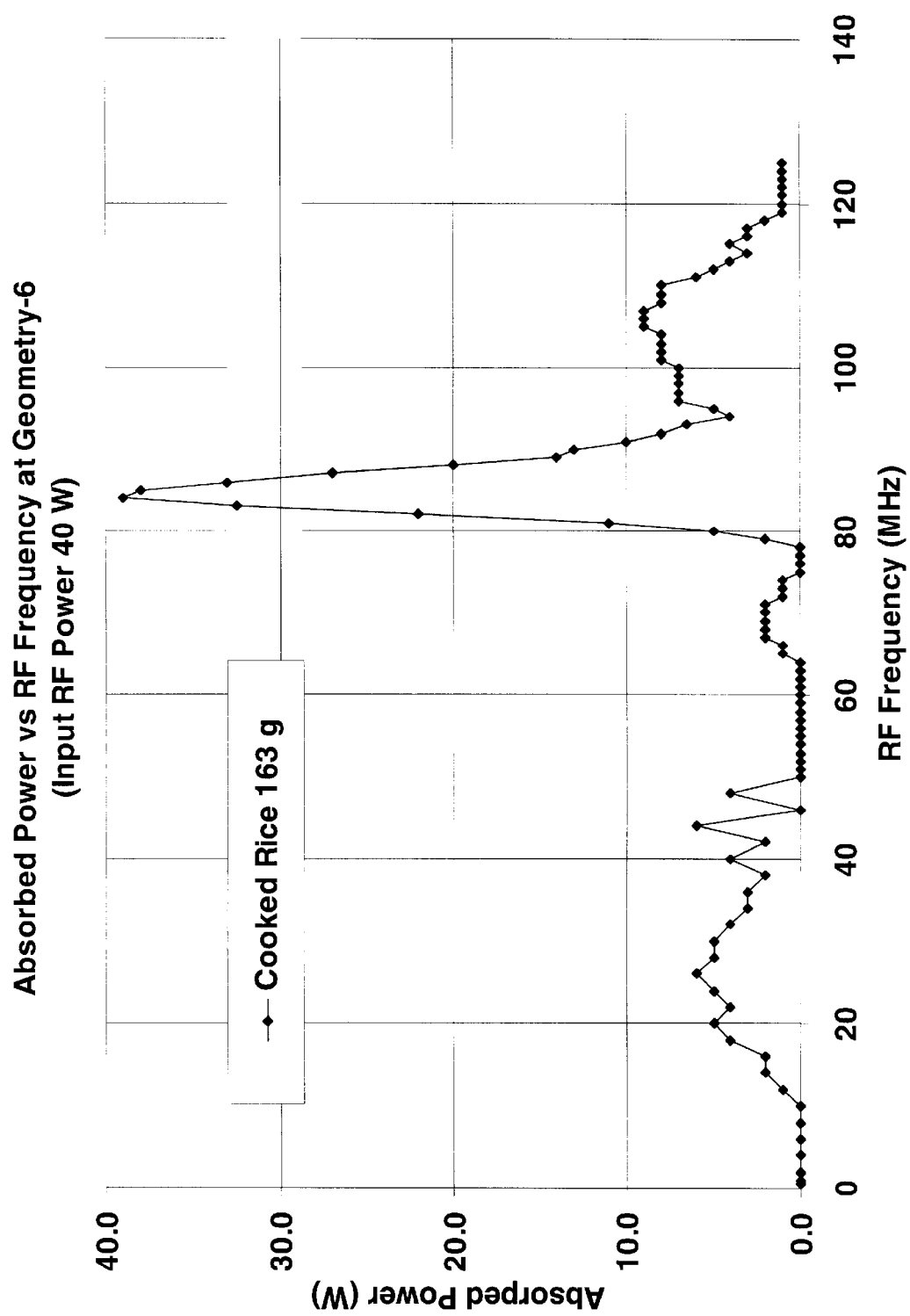
FIG. 7 is a plot of absorbed power versus frequency for a sample of cooked rice in a TEM Cell system of geometry-6 of the present invention.
Figure 8:
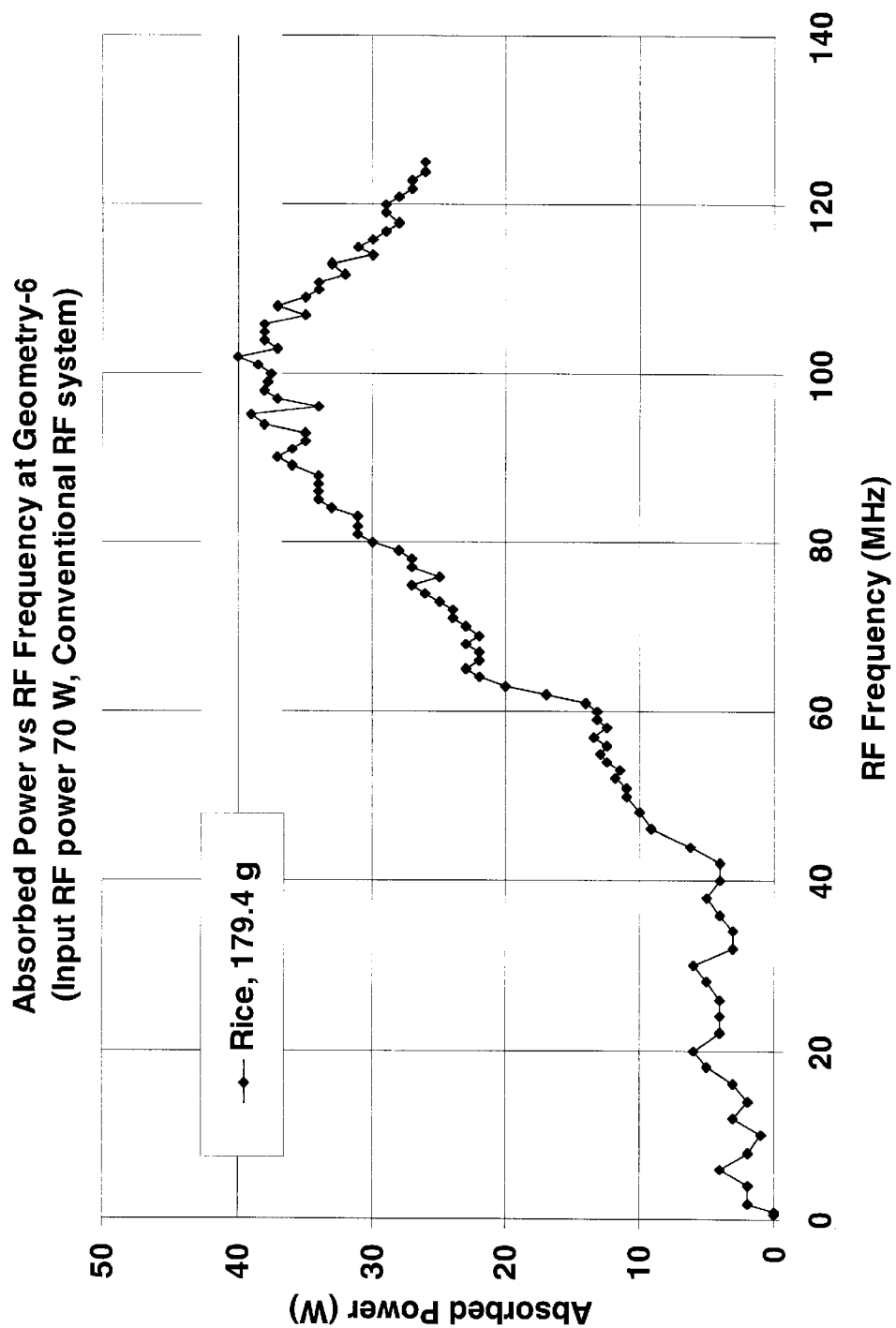
FIG. 8 is a plot of absorbed power versus frequency for a sample of raw rice in a TEM Cell system of geometry-6 of the prior art.

Results of RF experiments obtained with the TEM Cell 400 compared with the conventional TEM Cell 300 are summarized in Tables 2 and 3 below. Typical RF scanning curves for cooked rice (FIG. 7) and raw rice (FIG. 8) that show the same differences in use/conversion efficiencies are also included.

B. RF Processing of Various Agricultural Commodities

Extensive research using a RF dielectric heating system has determined the best frequency conditions to induce a rapid and efficient conversion of RF power into thermal energy. These measurements have been conducted with a group of host materials including: (i) berries (blackberries, raspberries, blueberries, strawberries); (ii) table grapes (Thompson Seedless, Red Flame Seedless, Black Beauty); (iii) agricultural soils (Yolo Loam, Yolo Fine Sandy Loam, UC mix soil, Carnation Greenhouse, sand); (iv) seeds (milo, tomato, pepper, peas, carrot, cotton, alfalfa, rice, corn); (v) spices (pepper, oregano, onion powder, garlic powder, paprika); (vi) beef (9%, 12%, 20% and 100% fat prime ground beef); (vii) milk (whole, 2% fat, non-fat); and (viii) wood (redwood; Douglas fir; pine); (ix) fresh fruit, including: pomes (Packham's pear, Granny Smith apple, Royal Gala apple); citrus (navel orange, tangerines, Eureka lemons, grapefruits); stone fruit (Modesto apricot, Bing cherries, Friar plums, yellow peaches, Fantasia nectarines); sub-tropical fruits (Hass avocado, kiwi); tropical fruits (mangoes, guavas, pineapples, bananas, papayas); (x) dry fruits (almonds, peanuts, pistachios, walnut, hazelnut); (xi) dehydrated fruits (raisin, prune, apple, apricot, banana); (xii) cereals (rice, wheat flour, mash potato powder); (xiii) fresh vegetables (tomato, potato, onion, pepper, garlic, asparagus); and (xiv) preserved food (peaches, apricot, pineapples, tomato).

These measurements also included water, air, saturated salt-water solutions, saturated sugar-water solutions, and vegetable oils as models of materials having different chemical properties and thus different dielectric properties (i.e., dielectric loss factors).

Figure 9:
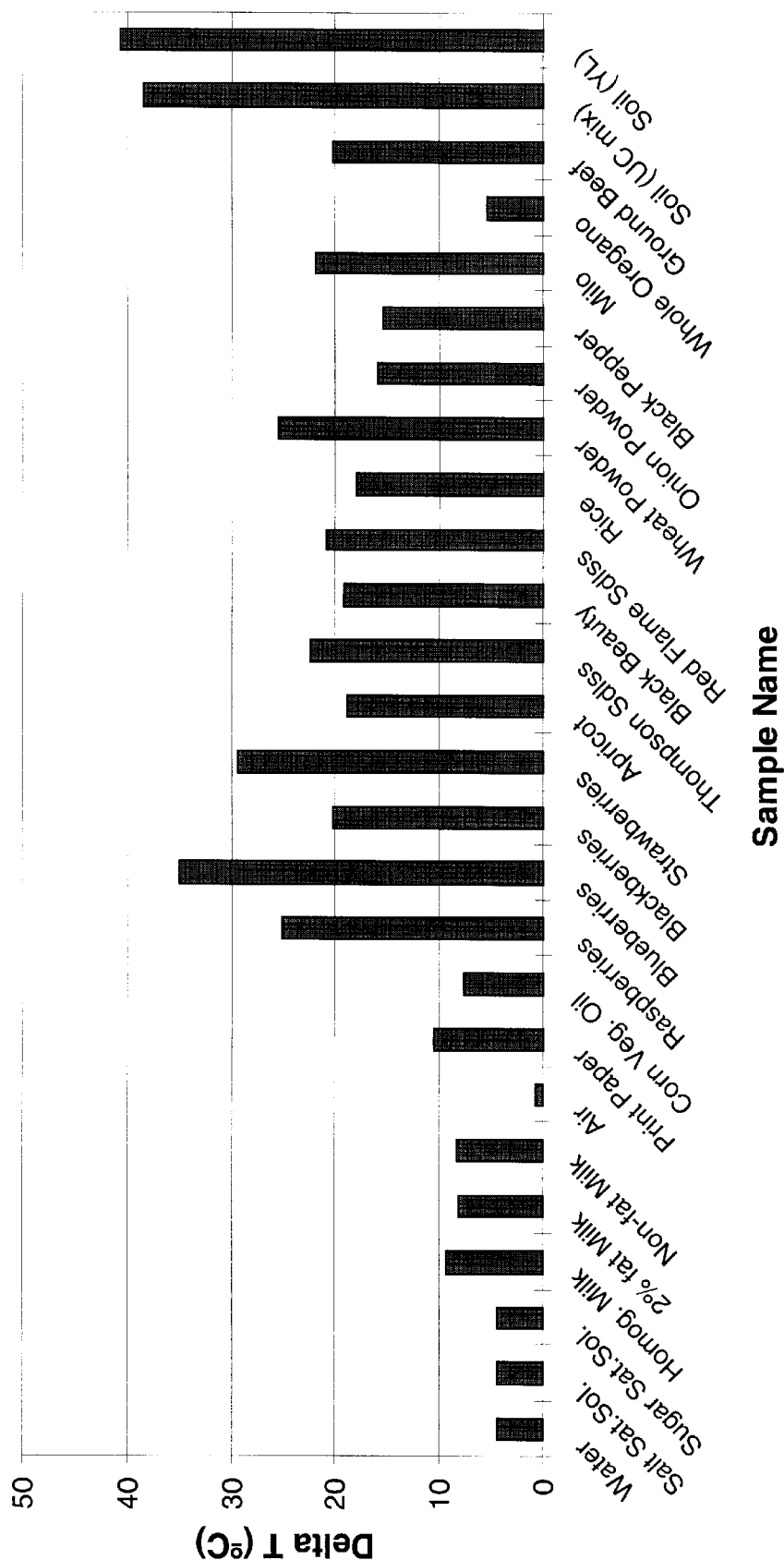
FIG. 9 depicts resonance RF-induced temperature increases for various samples at 86 MHz and 70 W for 1 hr.
Figure 10:
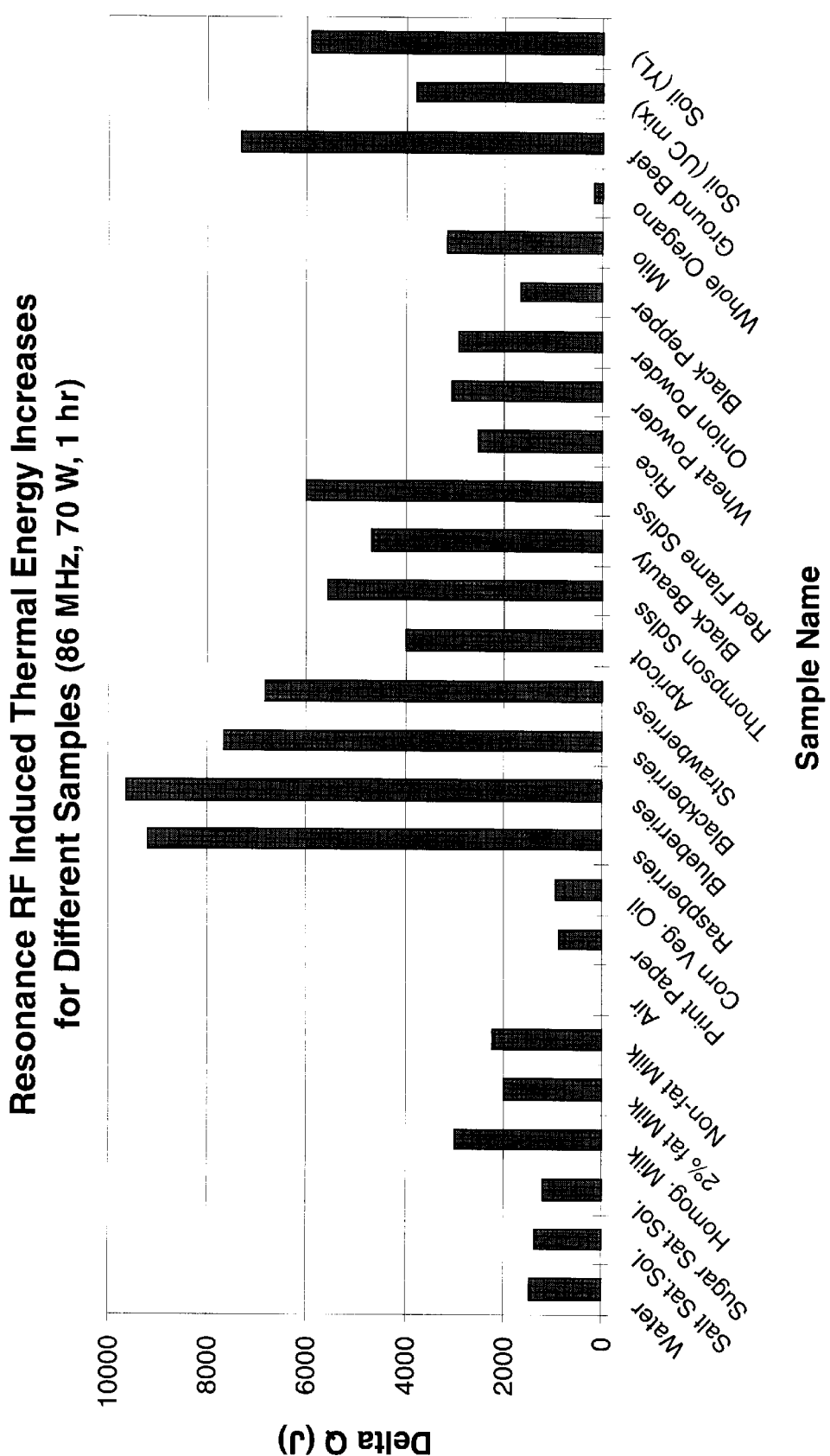
FIG. 10 depicts resonance RF-induced thermal energy increases for the samples of FIG. 9 at 86 MHz and 70 W for 1 hr.

The results of the above measurements were expressed as a function of RF power absorbed and RF operating frequency for all of the above mentioned materials, and allows one to define some of the RF operational parameters and RF applicators needed. The results of these measurements expressed as changes in temperature ($\Delta T$ in ° C.) and induced thermal power ($\Delta Q$; in Joules) are shown in FIG. 9 and FIG. 10, respectively.

Accordingly, one of skill in the art should appreciate that the method of the present invention may also be applicable to a wide variety of other agricultural commodities or valuable artifacts.

C. RF Frequency Behavior of Agricultural Commodities

Figure 11:
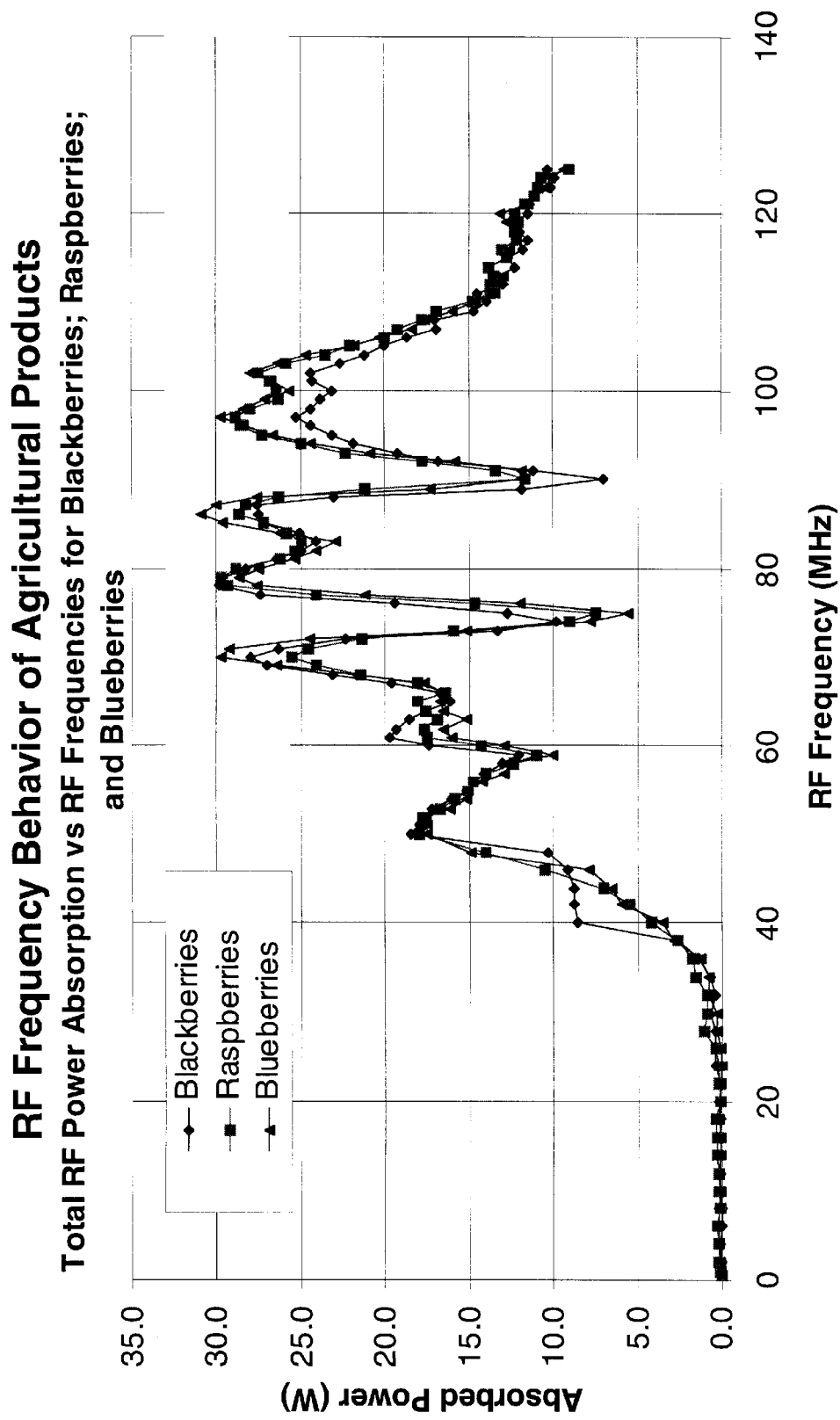
FIG. 11 is a plot of the RF frequency behavior of blackberries', raspberries', and blueberries' total RF power absorption.
Figure 12:
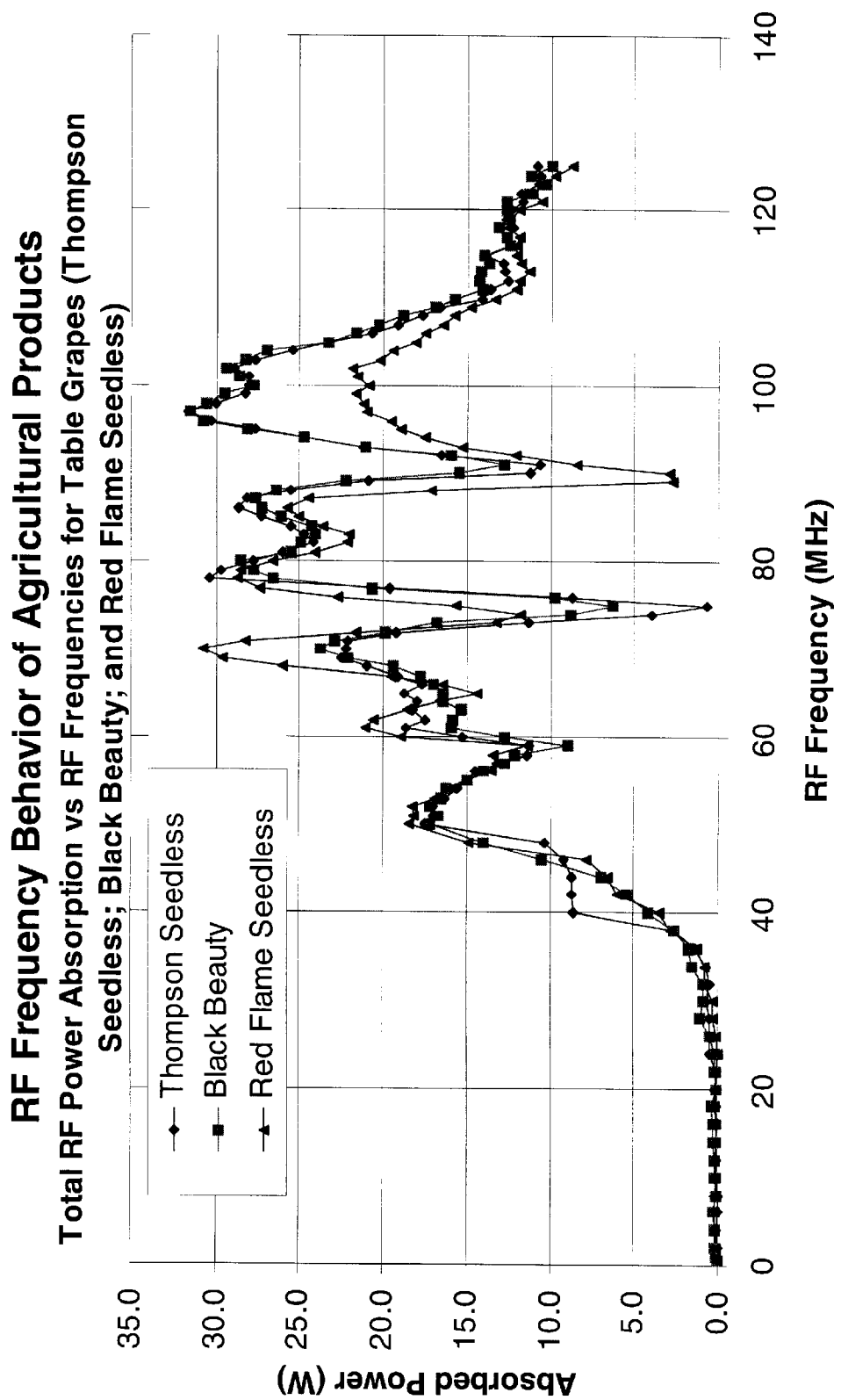
FIG. 12 is a plot of the RF frequency behavior of various table grapes' total RF power absorption.

In order to better define the matching or tuning of RF frequencies with the dielectric properties of several agricultural commodities likely to be treated with the RF method, a study was performed to measure the response of several agricultural commodities exposed to a range of RF frequencies capable of inducing thermal energy levels by absorbing and converting RF power to thermal energy. Results of these measurements are shown in FIG. 11 for blackberries, raspberries and blueberries; FIG. 12, for table grapes (Thompson Seedless, Black Beauty, and Red Flame Seedless); and FIG. 13 for soil and water.

These results clearly indicate that despite the general trend followed by these host materials, specific frequencies for certain commodities can be found to provide better efficiencies in the RF power absorption and its conversion to thermal energy (heat). Therefore, selecting an operating frequency for a certain product and geometry is believed to be a critical feature for maximizing the RF method and for an optimal condition to achieve the best process efficiency to induce a biocidal effects. This optimal condition will be product dependant.

Figure 13:
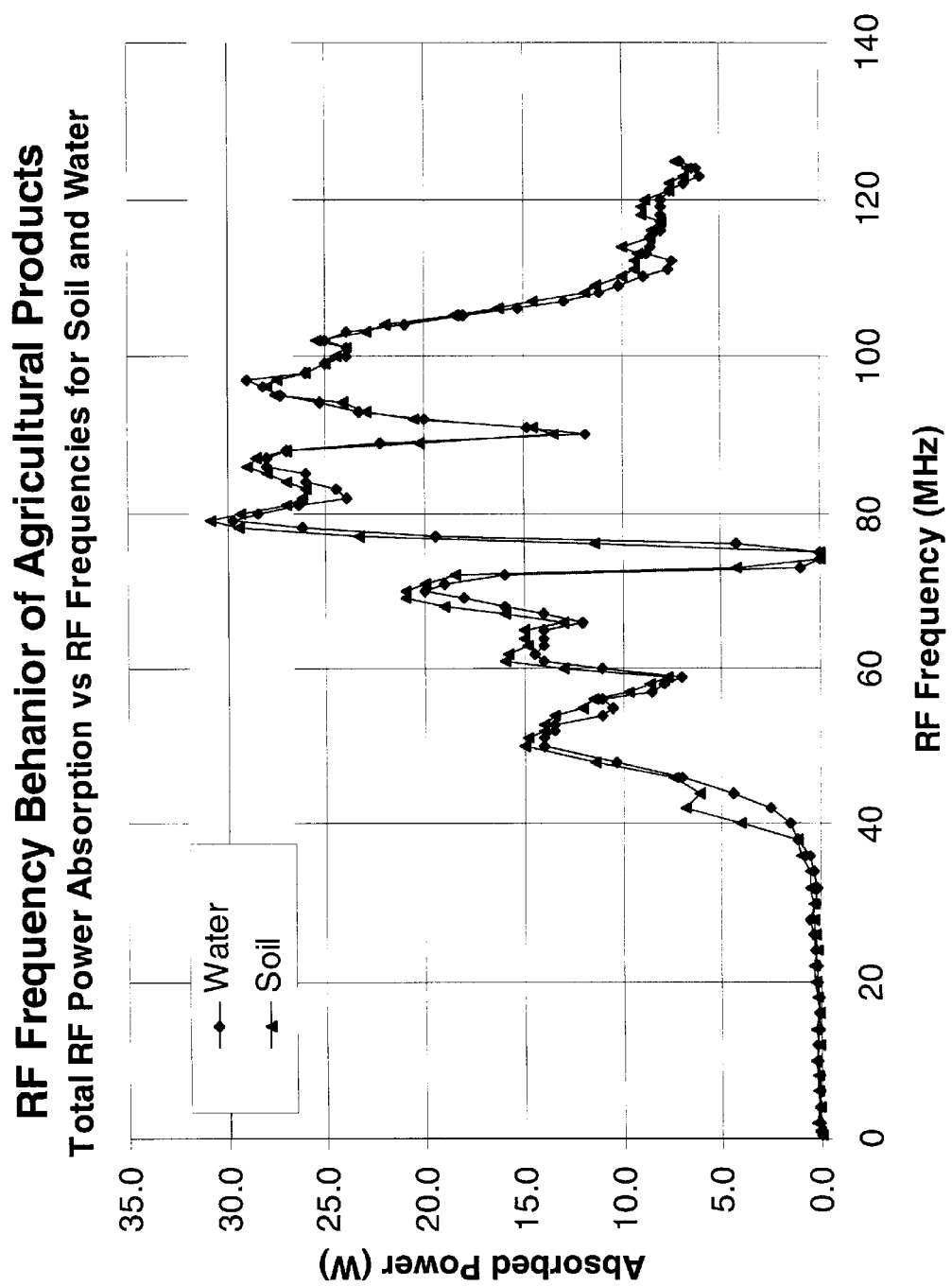
FIG. 13 is a plot of the RF frequency behavior of soil and water's total RF power absorption.
Figure 14:
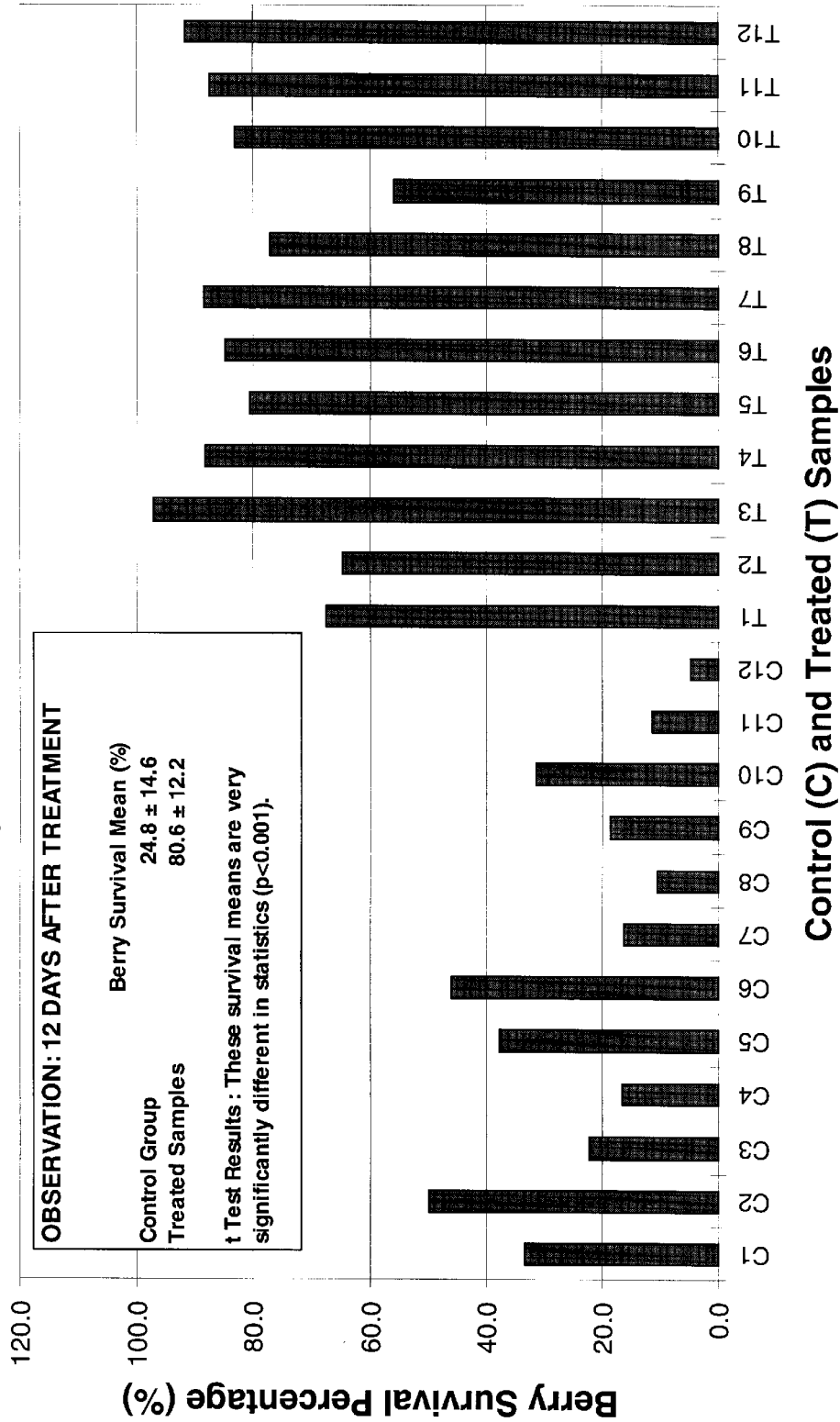
FIG. 14 is a histogram of the RF biostatic effect on Navaho blackberries using 1 MHz of 500 W power capacity system for 6 hrs.
Figure 15:
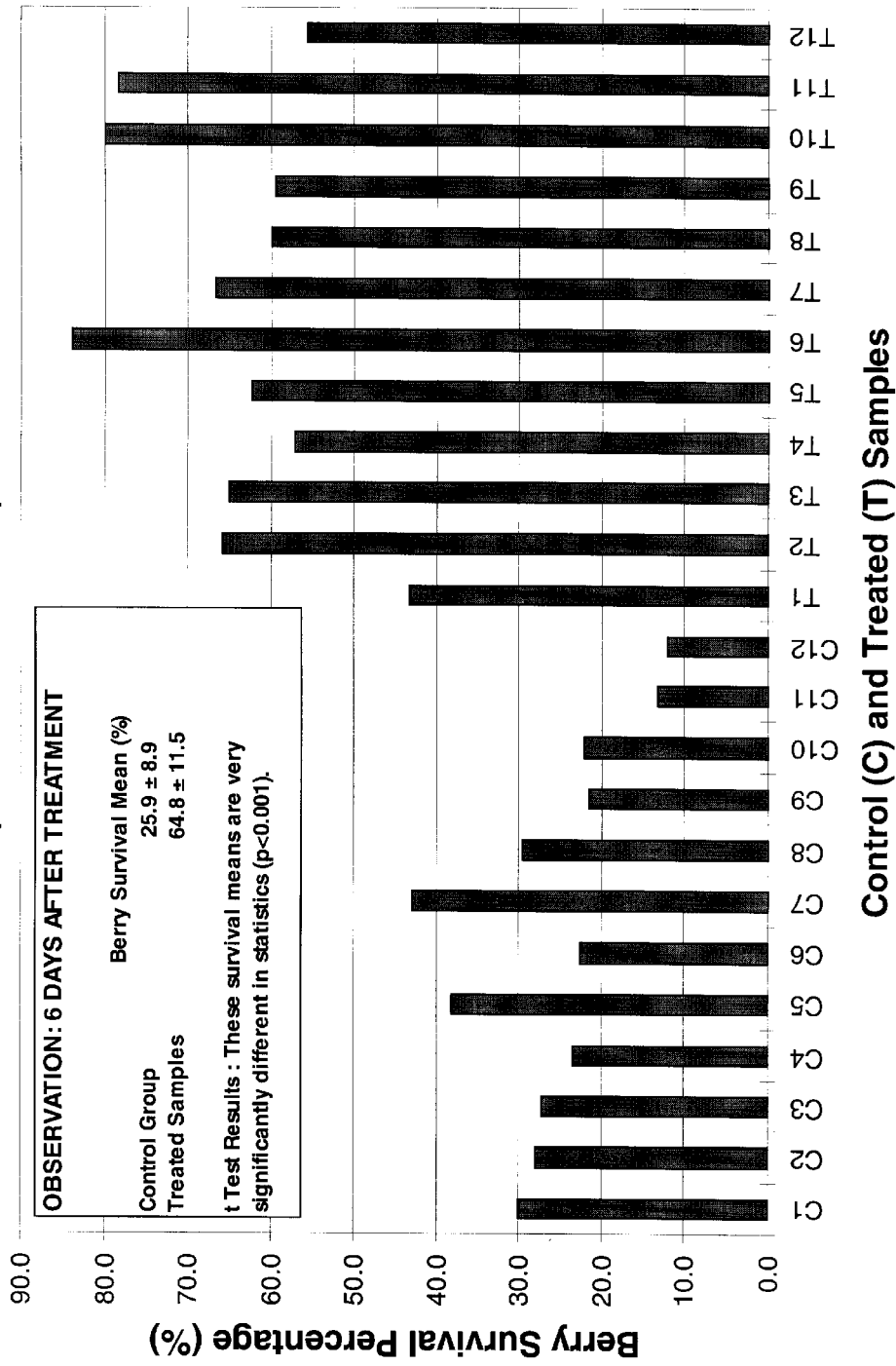
FIG. 15 is a histogram of the RF biostatic effect on Navaho blackberries using 1 MHz of 500 W power capacity system for 20 hrs.
Figure 16:
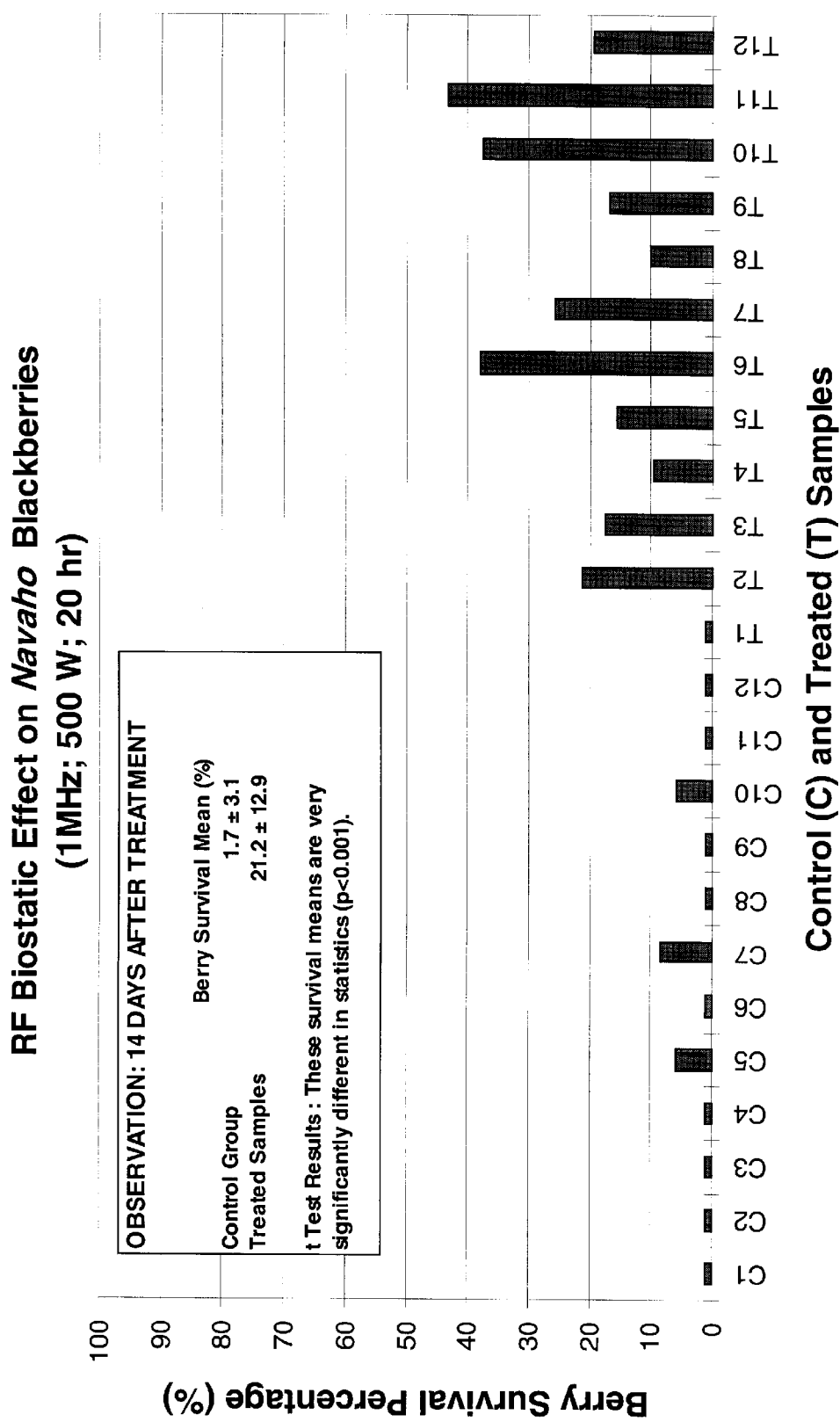
FIG. 16 is a histogram of the RF biostatic effect on Navaho blackberries using 1 MHz of 500 W power capacity system for 20 hrs.
Figure 17:
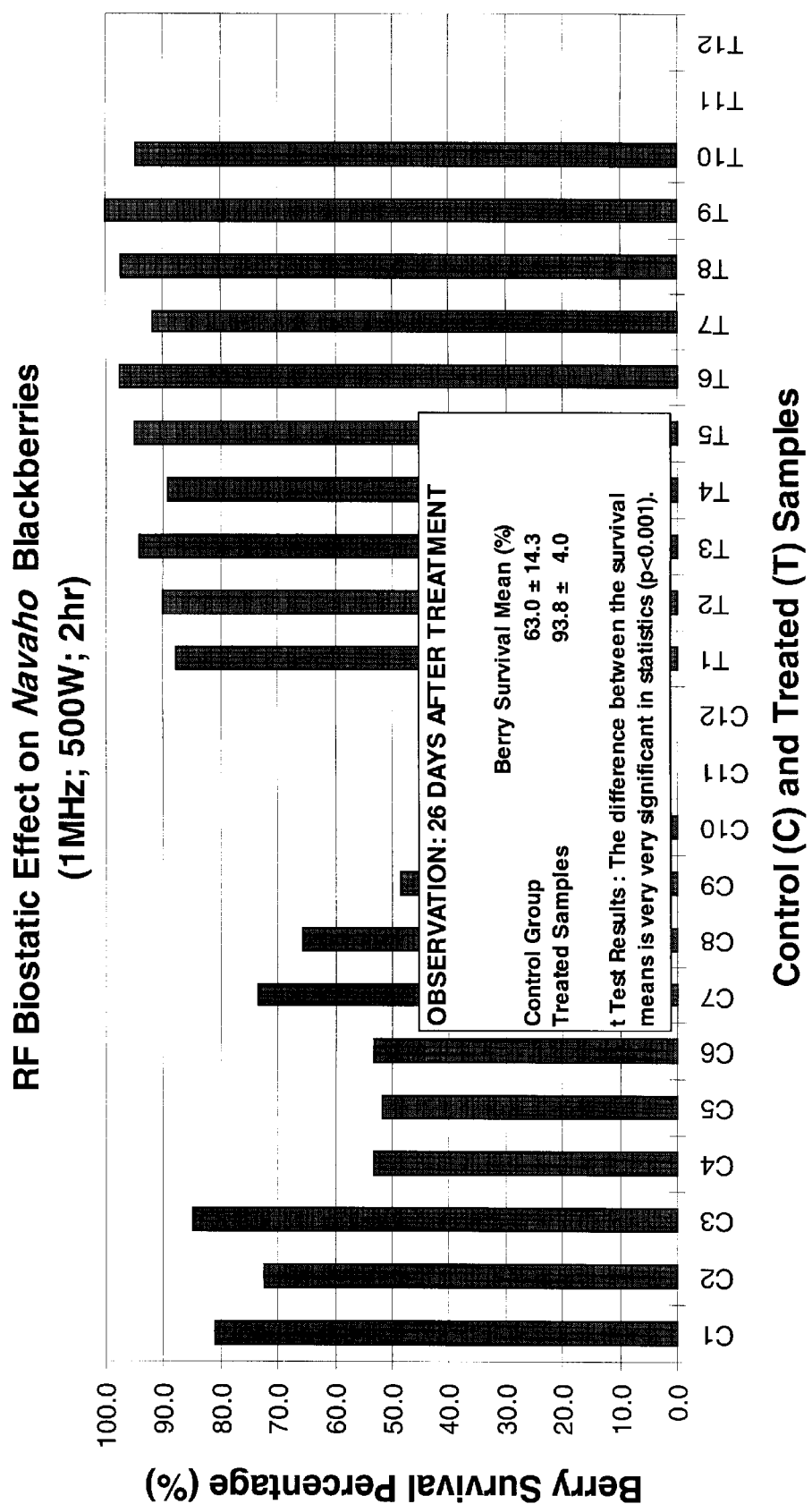
FIG. 17 is a histogram of the RF biostatic effect on Navaho blackberries using 1 MHz of 500 W power capacity system for 2 hrs.

For agricultural commodities, RF frequencies between 30 to 300 MHz, or at best 40 to 140 MHz, as shown in FIG. 11 through FIG. 13 are suggested as the optimal RF frequency band for an efficient operation of the RF method. In this RF region the characteristics of harmonic distribution suggests that the amplitude of the potential resonance peaks above 120 MHz will decrease as the RF frequency increases.

Finally, below 40 MHz, no thermal effects are expected and none were measured in these experiments. However, at 1 MHz, a biostatic effect has been demonstrated. This effect is similar to the fungistatic effect obtained with controlled atmosphere techniques already in use for long-term storage of a few fresh produce commodities.

D. Operative Thermal Windows

The RF process in one embodiment of the present invention is applied using a radio frequency field established with a parallel-plate electrode system using a narrow band of RF frequencies matched with the dielectric properties of a material. Under this condition, the absorption and conversion of RF power to thermal power can be accomplished efficiently and under set controls. Thus, RF techniques take advantage of the ability to couple a RF wave with the dielectric properties of a material. The net effect is to convert the RF power into thermal power within the treated material, homogeneously, rapidly, and with high energy-conversion efficiency.

Several materials may be used for processing with RF radiation to achieve disinfection and/or disinfestation without major thermal effects, and when operating under certain parameters. These include: human foods (fresh fruits and vegetables, dry foods, processed foods including canned foods, cereals; raw meats, poultry, and seafood; fruit juices, etc.); food additives (including spices); animal foods; plant seeds (including seeds for ornamental plants); wood and wood materials; waste materials (solid, liquid); plant materials (nursery commodities including soil and soil amendments); and agricultural soils. In wood materials, drying operations can also be realized.

Many of the materials are somewhat resistant to thermal energy applications and the limits are for the most part unknown. However, many materials are thermally sensitive and may be irreversibly affected, as they are materials with metabolic activity (i.e. some climacteric fruits, plant seeds, etc.), or have particular physical or chemical attributes (color, texture, aroma, etc.) that are essential for their marketing value, such as fresh foods. In order to obtain the maximum benefit of RF radiation with minimal impact on the material, the process must then take place within a low and a high thermal boundary as indicated in FIG. 1. In this manner, the process irreversibly affects the most thermal-sensitive contaminants present in the material, and causes only reversible changes in the host material itself.

The application of this operational concept requires knowledge of the thermal boundaries for each material. The boundaries of a thermal window are determined by measuring the thermal sensitivity of the host material and the thermal sensitivity of the contaminants.

As stated earlier and depicted in FIG. 1, infective organisms and insect/arachnid type contaminants have greater thermal sensitivity than their most common host materials. This is due to the greater complexity in their biological structures and principally on the existence of complex functional processes that are needed to sustain living organisms, such as respiration, energy production, and cell division for reproduction and repair. For insects and arachnids in all life cycles, a RF induced thermal level of 40–60° C. results in instant or delayed mortality or disruption of reproductive activity. For microbes, RF induced thermal levels of 55–70° C. results in greater than >4 $\log_{10}$ reduction levels (>99.99%). Lower thermal levels are also appropriate for lesser disinfection levels.

The experimental results shown in Table 4 indicate the thermal windows for host materials with RF radiation in the 0.5 to 250 MHz band.

As used herein, "disinfestation" refers to inhibiting the presence of insects and arachnids; "disinfection" refers to inhibiting the presence of microbes, such as bacteria.

According to Table 4, once a thermal window has been established, the introduction of RF radiation within these boundaries can take advantage of the thermal sensitivity of complex organisms present in the more resistant host material to perform disinfection and/or disinfestation of a variety of food and non-food materials.

Furthermore, the knowledge and use of a thermal window and the operational mode of RF radiation allows using smaller levels of thermal energy than those required with any other conventional heat process, including microwave radiation. The latter processes must either apply heat at the material's surface and often for long periods of time to allow for the entire volume to reach the required thermal level for disinfection and/or disinfestation, or it must use inherently higher energy photons in order to transfer energy to the host material. Both techniques run the risk of overheating the host material resulting in the loss of essential attributes.

The RF process, on the other hand, is a controlled, uniform thermal process. The thermal window 125 (of FIG. 1) is, in general, defined by the following parameters: (i) dielectric properties of the host materials; (ii) dielectric properties of the contaminant materials (i.e. microbial, insect, arachnids, protozoa, etc); (iii) thermal level for injurious (sub-lethal) effects to contaminant materials (this determines the low boundary of the contaminant's thermal window); (iv) thermal levels for lethal effects to contaminant materials (this determines the high boundary of the contaminant's thermal window); and (v) thermal sensitivity of the host material (this determines the high boundary 130 of the host's thermal window). As used herein, "injurious" levels are sub lethal effects and are those at which biological injuries are reduced that impede or prevent reproduction (i.e. enzyme inactivation; nucleic acid inactivation metabolic effects, etc.). Furthermore, "lethal" effects exclude immediate and delayed mortality.

Further still, the following set of factors apply to the configuration of the RF radiation field: (i) frequency (single or narrow band) (dielectric and/or inductive modes); (ii) electric field intensity; (iii) RF field geometry; (iv) host material geometry; (v) RF power; (vi) thermal time regimes for RF processing (discussed in section 0 below); and (vii),continuous RF or pulsed RF processing (discussed in 0 below).

The knowledge and the use of a thermal window for a material to be RF-treated allows for a defined level of induced thermal power that will maximize the decontamination effects while minimizing irreversible effects in the host material. As used herein, this is the "operational RF thermal window 125" (OTW 125) of FIG. 1 and is defined by both the thermal boundaries of the contaminant (insect, arachnids, and microbes) and the upper boundary 130 of the host material thermal window.

Many of the materials to be treated will be at an "ambient" temperature, thus fixing a maximum low boundary of the OTW 125. Accordingly, the OTW 125 must surpass the high boundaries for the contaminants in order to cause lethal or controlling effects in the contaminants, and be terminated below the high boundary 130 of the host material, to prevent irreversible changes in the host material. This operational concept is illustrated in FIG. 1.

For some materials, the high boundary 130 of the OTW 125 may depend on the intended use of the material, as in the case of dried or canned commodities in which few sensory properties or metabolic or physiologic attributes remain with respect to the original nature of the commodity. On the other hand, the low boundary 120 of the OTW 125 is clearly dependent on the thermal sensitivity of microbes, insects, arachnids, protozoa and the like. In practice, and using food as an example of a host material's OTW 125, the thermal sensitivity for insects, arachnids, and microbes (fungi, bacteria, and viruses) is greater than the thermal sensitivity of the host food commodity. Therefore, operating the RF radiation process within a thermal window that does not exceed the high boundary 130 for a host food commodity (to avoid or minimize potential effects) and allows for RF processing of the material and to achieve either or both disinfestation and/or disinfection effects while preserving its sensory and marketing attributes.

E. RF Induced Fungistatic (Biostatic) Effects

Another embodiment of the present invention uses RF radiation to induce a biostatic effect in a host material. Experiments based upon this embodiment of the present invention were conducted primarily with Navaho Blackberries of commercial quality, obtained from Hortifrut S. A. Blackberries were selected for these experiments because of their high spoilage rate due to the presence of several fungi among their natural flora. Immediately after receipt, berries were kept under refrigeration. Berries were treated with RF method within 1 day of receipt.

Groups of selected blackberries (controls and treated) consisting of 12 clamshells (commercial containers, geometry-20) each (i.e., 12 control clamshells, 12 treated clamshells), each containing—80 individual berries, were treated with a 1 MHz RF signal, and a 500 Volts/meter transverse electric field for 2 to 20 hours. The field was generated within an Amplifier Research Model TC3020 Transverse Electromagnetic Mode (TEM) Cell powered with a 500-Watt capacity source and terminated with a 1,000-Watt water-cooled 50-ohm load. The berries absorbed a small fraction of the RF energy, since there was no measurable temperature increase in the commodity. Furthermore, the terminator load absorbed most of the RF power.

Prior to the RF treatment, all blackberry samples were allowed to reach room temperature (~21–22° C.). The RF treatment was then conducted at room temperature for 2 to 20 hours. The time of treatment may be reduced with a proportionally larger RF power capability.

Immediately after the RF treatment was completed, the samples were transferred to refrigerated storage (4–5° C.) where they were stored during the entire observation period (up to 26 days). No temperature changes were observed immediately after RF treatment.

Observation of the post treatment berry conditions (i.e. presence of infection sites) was conducted daily. When infection sites were observed in either control or treated samples, each berry in each container was examined individually under laminar flow conditions, and the results were recorded and analyzed using statistical methods (t-test)

The results of these experiments on blackberries are summarized below in Table 5 and are shown graphically in FIG. 14 through FIG. 17.

A similar experiment with the same procedure indicated above was performed with 12 control clamshells and 12 RF treated clamshells. In that instance, the surviving berries were in a 5:1 ratio with the surviving control berries. One skilled in the art should appreciate that results obtained using TEM Cell 400 of the present invention will be comparable to those depicted in FIG. 14 through FIG. 17 and Table 5, but with less input power.

Further experiments were conducted to test this RF induced biostatic effect as a function of RF frequencies. These experiments were conducted with optimal coupling between the RF field and the product's dielectric loss factor and using TEM cell 300. Each experiment used 12 clamshells for control and 12 clamshells for RF treated Navaho blackberries (geometry-20). Results are shown in FIG. 18 through FIG. 20.

Figure 18:
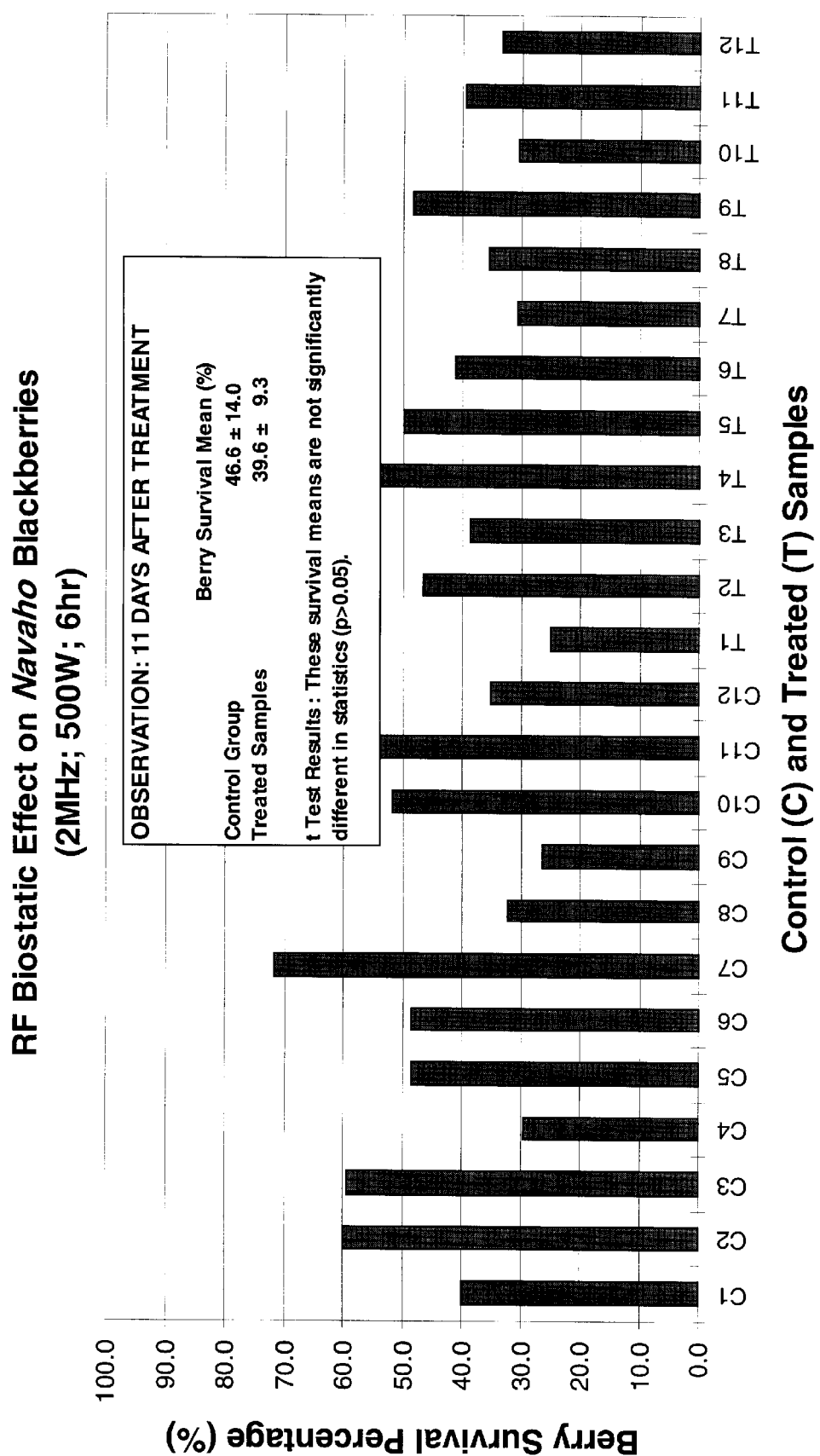
FIG. 18 is a histogram of the RF biostatic effect on Navaho blackberries using 2 MHz of 500 W power capacity system for 6 hrs.

At 2 MHz and at the same power level and time of exposure (500 W capacity system; 6 hrs.), the same type of treatment but at a 2 MHz frequency did not produce the same effects than at 1 MHz (FIG. 18).

Figure 19:
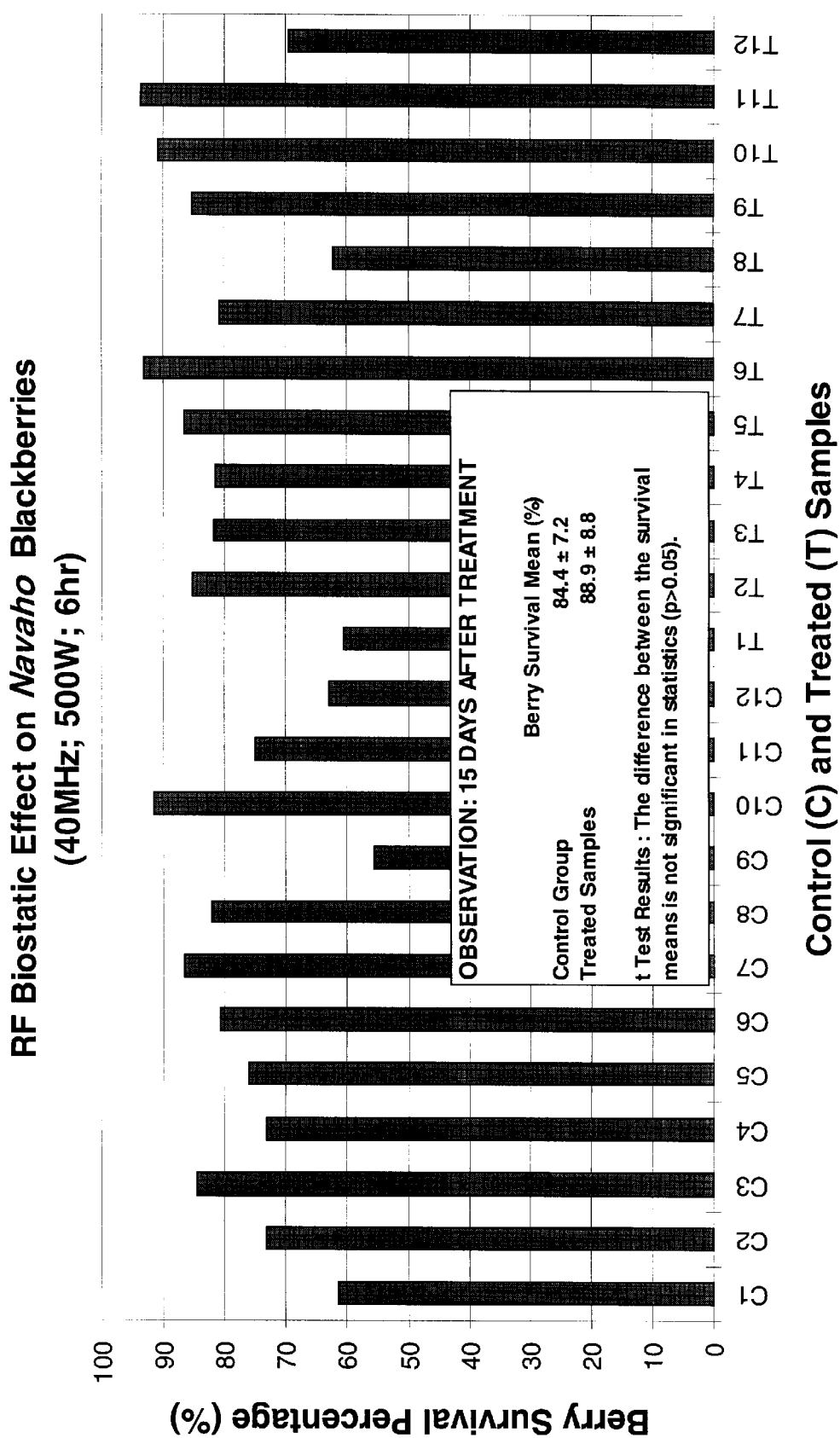
FIG. 19 is a histogram of the RF biostatic effect on Navaho blackberries using 40 MHz of 500 W power capacity system for 6 hrs.
Figure 20:
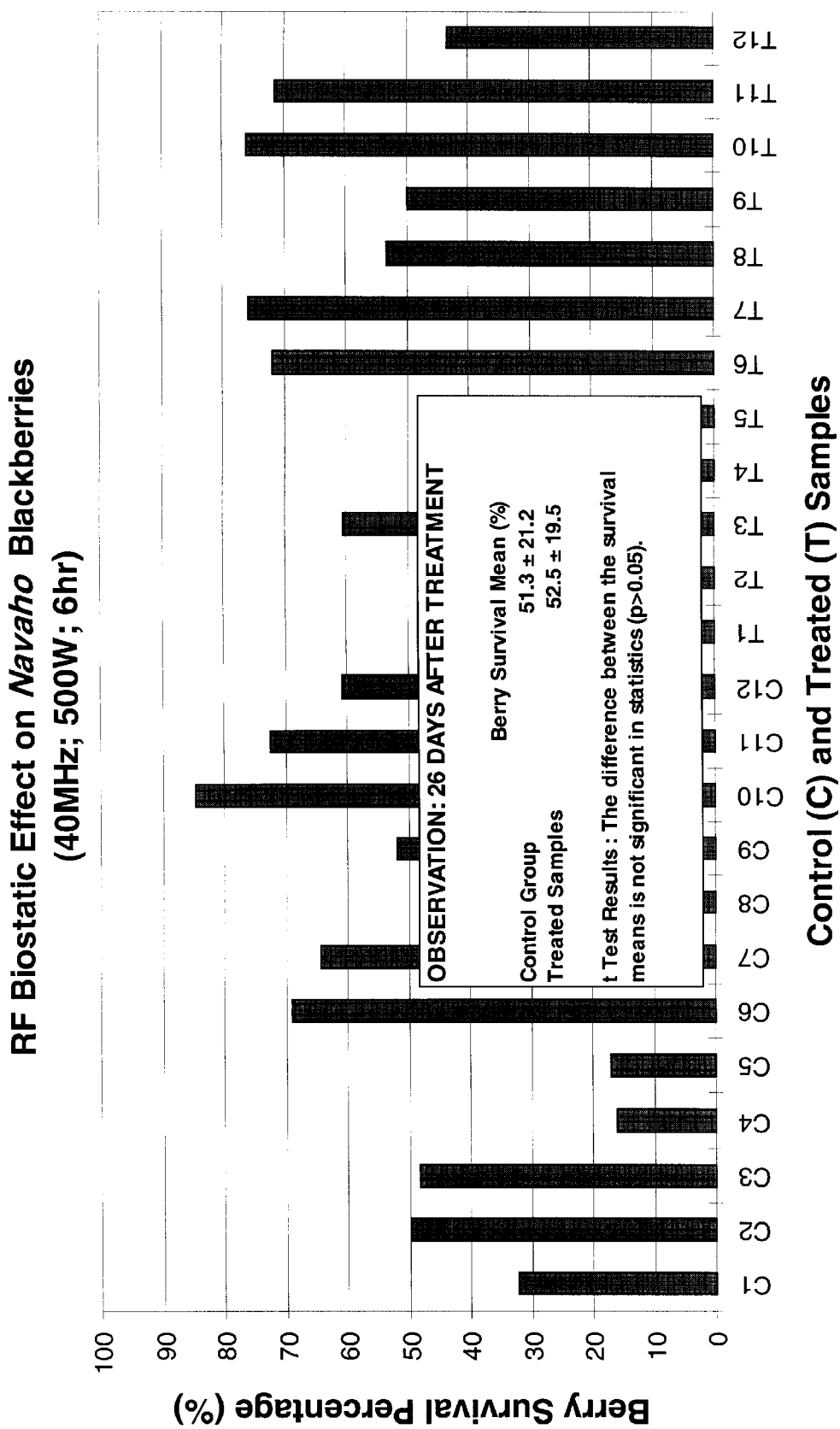
FIG. 20 is a histogram of the RF biostatic effect on Navaho blackberries using 40 MHz of 500 W power capacity system for 6 hrs.

Similarly, at 40 MHz and at the same power level and time of exposure (500 W capacity system; 6 hrs.), the same type of RF treatment did not produce the same biostatic effect as shown for the 1 MHz experiments (FIG. 19 and FIG. 20).

Therefore, a narrow band centered at 1 MHz, for blackberries yielded a positive biostatic effect induced by RF power. Again, one skilled in the art should appreciate that results obtained using TEM Cell 400 of the present invention will be comparable to those depicted in FIG. 18 through FIG. 20, but with less input power.

F. RF Induced Fungicidal (Biocidal) Effects

Another embodiment of the present invention uses RF radiation to induce fungicidal effects in host material. In this section, we indicate the effectiveness of the RF method to produce a fungicidal effect with large (greater than $10^5$ cfu/mL) inoculated levels of several fungi, when increases of the internally induced temperatures resulted in surface temperatures of ~45–55° C. ($\Delta T$=23–33° C.). Healthy, commercial quality blackberries (Navaho) were again obtained from Hortifrut S. A. Handling of the berries prior to RF treatment was similar to the methods described above. However, after RF treatment, and in order to facilitate and accelerate fungal growth, all berry samples (control and treated) were held at room temperature (~22° C.).

Selected blackberries (15–20 healthy, with no infected sites, firm and equally colored berries) were placed in 10-cm o.d. Petri dishes and inoculated with *Penicillium frequentans* (~15×$10^7$ cfu/mL and 5×$10^6$), with Botrytis cinerea (~$10^7$ cfu/mL), or with *Rhizopus stolonifer* (~5×$10^5$ cfu/mL). The Petri dish samples were covered with a lid and treated inside TEM Cell 300 with an increased distance between the radiating electrodes in order to maximize the electric field intensity (geometries 1, 2, and 3, with no appreciable difference in results). The RF method was applied at 67 to 70 MHz, which was the frequency range needed to maximize matching or tuning the RF field with the dielectric properties of the blackberries in the container geometry, and to better convert RF energy into thermal energy. The RF treatment was performed for 1 h with a low 60 W input power.

Greater than 4-log reduction (estimated) were obtained in all these experiments. Even when physical damage (crushing) of the blackberries eliminated any barrier for fungi to grow, extended shelf life was demonstrated at room temperature.

G. Blueberries, Raspberries, and Blackberries Containing a Natural Flora

We further demonstrated the effectiveness of the RF method to produce a fungicidal effect with various types of berries containing a natural flora, which consisted mostly of *Botrytis cinerea*, Rhizopus sp., and Penicillium sp.

Healthy, commercial quality blueberries (Brightwell; O'Neil); raspberries (Heritage); and blackberries (Navaho) were used. The berries were kept under refrigeration prior to RF treatment, equilibrated to room temperature prior to RF treatment, and kept at room temperature for observation after RF treatment.

Selected blackberries (~15–20 healthy, with no infected sites, firm and equally colored berries) were carefully placed in 10-cm o.d. Petri dishes, avoiding any physical stress on the samples. The Petri dish samples were covered with a lid allowing for sufficient space not to damage the samples, and treated inside TEM Cell 300 with an increased distance between the radiating electrodes in order to maximize the electric field intensity and the RF-to-thermal power conversion (geometries 1, 2, and 3, with no appreciable difference in results). This time, the RF method was applied at 86 MHz (tuning RF field with product geometry) for 1 hour at 70 W input power. The results of these experiments are summarized in Table 6.

Greater than 4 days of room temperature (~22° C.) storage were obtained in all these experiments indicated the ability of the RF method to induce a lethal effect on the natural flora present in these samples. Since no physical damage was allowed during these experiments, the extended shelf life demonstrated at room temperature, with no visible sensory or physical effects on the berries, demonstrated the efficacy of the RF method to inactivate spoilage fungal organisms. Again, one skilled in the art should appreciate that results obtained using TEM Cell 400 of the present invention will be comparable to those depicted in Table 6, but with less input power.

Several experiments were further conducted with berries containing a natural flora demonstrating the reproducibility of the above results.

H. Thermal-Time Regimes for RF Processing

As discussed earlier, many host materials exhibit a high sensitivity to the application of thermal energy. Foods (i.e. fresh fruits; fresh vegetables; some processed fruit juices; raw meats, poultry, pork and seafood; eggs, etc.), certain non-food materials such as biological fluids (blood products, plasma, etc.), cell and culture preparations, etc. all have low tolerance to heat processing.

In these types of host materials, thermal energy may cause changes in sensory as well as chemical (i.e. nutritional) properties. The latter attributes are critical for the marketability of the product and thus, there are several limitations when large-scale, commercial applications of thermal processing are considered.

Despite these limitations, many host materials are currently treated with controlled levels of heat simply because no other alternatives are currently available. Such is the case with some tropical fruits such as mangoes (for quarantine purposes), with pasteurized fruit juices, and with pathogen inactivation in blood products.

Most of the current uses of thermal processing rely on the application of heat without taking advantage of the dynamics of the thermal process (i.e. heat distribution and heat losses). For the most, they also ignore the existence and/or the use of the natural phenomena that allow thermal-sensitive materials to sense, respond, and react to changes in ambient temperature and/or to the changes to their body temperature (i.e. evaporative cooling).

We have demonstrated that changes and damage to essential properties are greatly minimized when the rate of thermal processing and the total thermal energy applied are kept between some appropriate boundaries. These boundaries need to be matched with the host material's thermal window.

Therefore, the thermal-time regimes determine the rate of heating. Consistent with the present invention, the thermal-time regimes refer to the process of combining appropriate thermal processing parameters such as thermal energy intensity or power with the time of application. Controlling the rate of heating allows delivering the same amount of energy to achieve an intended effect but at different time intervals. Extended time intervals allow for the material to adjust to thermal energy input including distributing heat, losing heat by radiation and evaporative cooling and the likes. In this manner, potential damaging changes can be minimized or entirely avoided.

Several commercial processes for liquid milk exist today in which high temperature is used for short times (UHT process or ultrahigh temperature) because it accelerates pathogen inactivation (low threshold) while it controls the extent of some rate-determining steps leading to oxidative reactions that causes degradation of flavors and/or aromas. While the UHT process do cause some nutritional losses, the fact that there is an increased sensitivity of the microbial flora to this type of processing with elevated temperatures, minimizes the time for some less sensitive oxidative reactions taking place.

The UHT process's rationale is exercising a control over the dynamics of both the disinfection and the chemical oxidation processes while taking advantage of the differential elapsed times required for accomplishing these processes.

The application of this concept to address the needs for microbial, insect, and arachnid decontamination in various fresh foods, processed foods, and in other sensitive host materials such as valuable artifacts, is well suited. However, the rationale was extended to a reverse process in which, consistent with the present invention, we incorporate the host material's own heat dissipation processes as a means to utilize the differential sensitivity between contaminant and host. In particular, this is the case when dealing with a higher-sensitivity contaminant (i.e. insect, arachnids, and microbes) present in a low heat tolerance host material (i.e. fresh foods).

This approach, as used herein, is referred to as a Low Power—Long Time RF Process LPLT process). The LPLT process keeps the rate of thermal energy application to a thermal-sensitive material low over a long time. This is especially appropriate for thermally sensitive materials that exhibit stress expressed as physiological changes as well as sensory (i.e. cosmetic) effects. Important attributes such as degradation of texture and aroma are critical when these materials are exposed to thermal energy. If the purpose of thermal processing is to decontaminate these materials (i.e. disinfect and/or disinfest), the LPLT RF process has been proven to be effective to decontaminate thermally sensitive fresh fruits (or fresh foods like meats, poultry, seafood) while keeping the host material's sensory and marketing attributes (see Tables 7 and 8, below).

When LPLT RF processing is used in fresh fruits, thermal energy is induced with the application of low RF power (<1 W/g of material), but over a period of time (minutes to hours) that allows slow warming of the different tissues. In this manner we avoid sudden expansion of tissues and liquids and prevent rupturing tissues. The total energy applied is sufficient to cause immediate or delayed mortality in insects and arachnids, impede reproduction in insects and arachnids, and/or the inactivation of microbes, with minimal physical and chemical effects in the host material.

For fresh fruits and vegetables, as an example of thermal-sensitive commodities, the rate of application is defined by several physical, chemical, and/or biological factors such as: heat capacity; thermal window (see section 0); water content (for evaporative cooling purposes); thermal window of insect and arachnids (for disinfestation or quarantine purposes); thermal window of microbial contaminants (for disinfection or pasteurization); thermal properties of packaging materials; rate of metabolic respiration (for fruits and vegetables); and hardness (mechanical strength) of materials.

Experimental results supporting this concept and using raspberries, blackberries, and blueberries, which are host materials of a particularly high thermal sensitivity, are given in Table 7 and Table 8 below. In Tables 7 and 8, the observation for damage was done immediately after RF exposure and after several days in room temperature (RT) or refrigerated storage (RS). Both sets of observations were compared with non-treated controls. Furthermore, the geometries used were geometries 1, 2, and 3, with no appreciable difference in results.

Table 8 summarizes the results where the sample consists of 160 grams of raspberries in clamshell geometry and the RF radiation is at 116 MHz.

Of particular note are the results in Table 8 for raspberries at 116 MHz for 21.7 minutes, 37.5 minutes and 57.8 minutes at varying levels of inputted power where no damage was found. One skilled in the art should appreciate that for an 160 gram sample raspberries and an input power of 40 watts, the electric field strength is of the order of 10–20 V/cm, and well below the disclosed 500 V/cm of the '636 patent.

The LPLT RF process may be particularly applicable in disinfecting raw foods such as meats, poultry, pork, and seafood. The LPLT process can prevent sensory (i.e. discoloration) and/or nutritional changes (i.e. losses of thiamine, vitamins, etc.).

I. Pulsed Techniques

The effects of using pulsed power techniques to affect the viability of living organisms are well known. For example, U.S. Pat. Nos. 5,364,645 and 5,607,711, both herein incorporated by reference, disclose applications of pulsed ultraviolet techniques.

In the context of RF radiation, pulsed RF consists of delivering short duration RF 10 energy in time intervals approaching sub-microsecond ($<10^{-6}$ s) time intervals. In this manner, the RF power levels used in the development of this technology will experience significant increases. Nevertheless, the same kinetic enhancement effects associated with high peak power techniques will provide increased efficiency in disinfection and disinfestation applications. This is particularly important when a high thermal-sensitivity contaminant such as insects, arachnids, and microbes are the intended target of application in more thermal-resistant host materials (foods and other materials). Accordingly, one skilled in the art should appreciate that pulsed RF effects will result in an increased efficiency in achieving decontamination (disinfection and/or disinfestation) in sensitive host materials.

Consistent with the present invention, a pulsed RF process for disinfection and/or disinfestation will take advantage of the higher sensitivity of living organisms to short-duration pulses of energy. Specifically, when short-duration thermal pulses are used, living matter is exposed to a thermal energy-transfer process that overwhelms any mechanism of thermal energy transport and dissipation, any repair mechanism, and any thermal cooling effects including evaporative cooling. Living matter is thus exposed to energy levels that causes permanent and irreversible (non-repairable) effects.

One skilled in the art will appreciate that the positive, controlling effects already demonstrated with the use of conventional, low power RF techniques might be greatly enhanced by using a repetitive, short spaced, high energy density process provided by pulsed RF.

J. Conclusion

Radio frequency (RF) power applied with parallel plate electrodes at specific frequencies in the 0.1–1,000 MHz band of the electromagnetic energy spectrum, was utilized to (1) generate fairly homogeneous electromagnetic effects (0.1–10 MHz), and (2) controllable levels of thermal energy on various commodities at frequencies greater than 30 MHz. These effects were induced on the surface and inside the mass of different types of highly perishable materials. The low frequency (0.1–10 MHz) electromagnetic effects caused no measurable thermal effects but slowed down the development of spoilage organisms (i.e. biostatic effect). Because non-thermal effects were induced, the biostatic effect has no potential for sensory and/or physiological changes in the commodities. At higher frequencies (>40 MHz), the induced thermal energy levels were sufficiently high to cause—homogeneously throughout the host material—a lethal, controlling (i.e. biocidal) effect on contaminating organisms. By selecting an appropriate RF power level and time of treatment, the induced thermal energy levels were kept below those that cause deleterious effects on the host materials. In this manner, the biocidal effect can be achieved thermally while preserving the keeping and marketing qualities of perishable host materials.

Thermal energy is well known to cause biocidal effects on organisms as well as irreversible changes in the sensory properties of fresh foods. However, the RF method operates within the boundaries of a "thermal window," that is, it uses the differential thermal-energy sensitivity between living organisms (highly heat sensitive) and the more heat-tolerant properties of host materials (less heat sensitive). The optimal operation of the RF method is just above the lower end of the thermal window in which the induced thermal energy levels produce lethal effects on organisms, principally fungi and bacteria. Furthermore, the operation of the RF method allows keeping the induced thermal energy levels below the level where unacceptable changes on the quality and keeping characteristics of a host material are produced.

The disclosed RF method can replace or minimize the use of chemical techniques (i.e. pesticides), and significantly improve or overcome the limitations that are encountered when conventional heat-treatment techniques (conduction and convection) are used for the treatment of fresh, perishable agricultural commodities. The RF method is efficient in using the lower levels of the thermal window where the living organisms are susceptible to thermally induced mortality. This is due to their greater biochemical and physiological complexity when compared to the structural and functional properties of fresh foods. The destruction of microorganisms is initiated by the thermal denaturation (inactivation) of proteins, enzymes, or genes essential to reproduction. The RF method is also based upon the limited thermal tolerance existing in fresh produce in general. It has been shown to be efficient and apt for treating highly perishable and thermally sensitive agricultural commodities. Despite their heat sensitivity, these commodities have considerable less metabolic or physiological complexity than contaminating organisms and, therefore, tolerate higher inputs of thermal energy. Accordingly, the RF method combines the ability of modern RF electronics to be tuned to the dielectric properties of agricultural commodities and to operate within the host material's thermal window.

Application of the above approach has been demonstrated on various products including highly perishable and highly temperature-sensitive fresh fruits (i.e. raspberries, blackberries, blueberries). A variety of berry samples with either natural flora and with samples inoculated with large microbial levels (up to $10^7$ cfu/mL), were used to demonstrate the effectiveness and the reproducibility of the RF method. This was achieved without sensory and/or physiological changes to the berry samples. These samples were kept at room temperature storage for up to 2 weeks.

One skilled in the art will appreciate that this technological approach has efficiency, throughput, practical and logistical advantages over many existing processes and will allow implementation of new strategies benefiting agricultural and urban interests. These treatment systems will be non-chemical, energy efficient, with high throughput, with simultaneous microbial and possibly insect and arachnid controls, simple to operate, and of modular design.

Although the invention was described with respect to fresh fruit, one skilled in the art will appreciate that the above criteria may also he applicable in: disinfecting and disinfesting plant and ornamental products without affecting plant physiology; disinfecting and disinfesting plant seeds while preventing any biological activity effects (i.e. germination); and disinfecting processed liquid and solid foods without sensory changes and/or nutritional losses. Furthermore, the invention disclosed herein may also be applied to the inactivation of viruses in many different media, including some foods and biological products (i.e. blood derived products) as a non-chemical technique leading to viral inactivation.

One skilled in the art will also appreciate that many other commodities such as agricultural soils, dairy products, and processed fruits and vegetables are also candidates for RF processing using a similar approach. In most cases, the RF method has the potential to replace or minimize the use of chemicals and to better keep the sensory properties of processed foods as it is based on the use of limited, but efficient, thermal energy levels. Overheating of the host material, with the subsequent losses in organoleptic and nutritional quality, can be minimized or avoided. Further still, the RF method may be applied to valuable artifacts such as art objects or antique books, in order to preserve the artifact's sensory and storage properties.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

| Geometry | Dimensions (mm) (Depth-Width-Length) | Host Commodities | Comments |
| --- | --- | --- | --- |
| 1 | 22-142-142 | Seeds, Wood, Soil, Ground Beef, Milo | No Insulation |
| 2 | 17-142-142 | Wood, Soil, Milo, Seeds | No Insulation |
| 3 | 19-150-150 | Seeds, Wood, Soil, Dried fruits, Insects, Packing Material | $4\pi$ Styrofoam insulation |
| 4 | 90-120-120 | Whole fresh fruits (apple, orange, pear) | $4\pi$ Styrofoam insulation |
| 5 | 50-170-105 | Strawberries | $4\pi$ Styrofoam insulation |
| 6 | 47-115-130 | Strawberries, raw and cooked rice | $4\pi$ Styrofoam insulation |
| 7 | 50-580-165 | Raw rice (1 bag) | $4\pi$ Styrofoam insulation |
| 8 | 57-173-110 | Berries | $4\pi$ Styrofoam insulation |
| 9 | 40-90-110 | Wastewater, fruit juices | $4\pi$ Styrofoam insulation |
| 10 | 20-50-150 | Milk, apple juice, insects | $4\pi$ Styrofoam insulation |
| 11 | 35-125-135 | Cattle feed, Dairy mix, Cheese | $4\pi$ Styrofoam insulation |
| 12 | 73-125-135 | Strawberry Clamshell | $4\pi$ Styrofoam insulation |
| 13 | 47-225-310 | Lunchbox | $4\pi$ Styrofoam insulation |
| 14 | 70-530-415 | Berries box | $4\pi$ Styrofoam insulation |
| 15 | 35-190-190 | Whole fresh fruits | $4\pi$ Styrofoam insulation |
| 16 | 21-91-108 | Fungi and yeast | $4\pi$ Styrofoam insulation |
| 17 | 70-220-530 | Berries Box | $4\pi$ Styrofoam insulation |
| 18 | 40-110-90 | Bread | $4\pi$ Styrofoam insulation |
| 19 | 45-145-160 | Berry clamshell (U.S.) | $4\pi$ Styrofoam insulation |
| 20 | 45-170-170 | Berry clamshell (Chile) | $4\pi$ Styrofoam insulation |
| 21 | 70-150-170 | Whole fresh fruits | $4\pi$ Styrofoam insulation |
| 22 | 65-185-150 | Tree leaves | $4\pi$ Styrofoam insulation |
| 23 | 35-230-120 | Small tree's roots & soil | $4\pi$ Styrofoam insulation |
| 24 | 95-185-150 | Small tree's leaves | $4\pi$ Styrofoam insulation |
| 25 | 110-755-290 | Whole Small tree | $4\pi$ Styrofoam insulation |
| 26 | 190-555-285 | Whole Middle tree | $4\pi$ Styrofoam insulation |
| 27 | 195-810-340 | Whole Large tree | $4\pi$ Styrofoam insulation |

TABLE 2

| System (Material) | Temperature Gradient (° C.) Processing Time (min) | | | Absorbed Power Ratios $R_{ab}$ | Comments |
|---|---|---|---|---|---|
| | 30 | 60 | 120 | | |
| TEM Cell 300 (Raw Rice) | 8 | 11 | 24 | 48% | Low ΔT Low RF Power Absorption |
| TEM Cell 400 (Raw Rice) | 14 | 26 | 43 | 98% | High ΔT and High RF Power Absorption |
| TEM Cell 400 (Cooked Rice) | 15 | 27 | 52 | 99% | High ΔT High RF Power Absorption |

TABLE 3

| System (Material) | Temperature Gradient (° C.) Time of Processing (3 min) | Absorbed Power Ratio $R_{ab}$ | Comments |
|---|---|---|---|
| TEM Cell 300 (Wastewater) | 29 | 49 | Low ΔT Low RF Power Absorption |
| TEM Cell 400 (Wastewater) | 63 | 95 | High ΔT and High RF Power Absorption |

TABLE 4

| Host material | Low Boundary (° C.) (Ambient) | High Boundary (° C.) | Intended Effect |
|---|---|---|---|
| Fresh Fruits | 15–30 | 40–60 | Disinfestation Disinfection |
| Fresh Vegetables | 15–30 | 40–60 | Disinfestation Disinfection |
| Dry Foods (Grains & Cereals) | 15–30 | 70–90 | Disinfestation Disinfection |
| Processed Foods | 15–30 | 70–90 | Disinfestation Disinfection |
| Raw Meats | 15–30 | 60–75 | Disinfection |
| Raw Poultry & Pork | 15–30 | 60–75 | Disinfection |
| Seafood | 15–30 | 60–75 | Disinfection |
| Dairy Products | 5–30 | 40–70 | Disinfection (Pasteurization) |
| Food Additives (&. Spices) | 15–30 | 70–90 | Disinfestation Disinfection |
| Wood & Wood Products | 15–30 | 50–90 | Disinfestation Disinfection Drying |
| Waste Materials (Solid & Liquid) | 15–30 | <90 | Disinfection |
| Soils & Amendments | 10–20 | 50–80 | Disinfestation Disinfection |
| Plants | 10–30 | <60 | Disinfestation |
| Plant Seeds | 10–30 | <75 | Disinfestation Disinfection Enhanced Biological Activity |
| Art Objects | 10–30 | <90 | Preservation by Disinfection and/or Disinfestation |

TABLE 5

| Sample | RF Treatment | Observation Date-Treatment Date | Statistical results as percent survival (percent Gain of Treated Samples) |
|---|---|---|---|
| Navaho Blackberries | 1 MHz 500 W 6 hrs. | +12 days | Control: 24.8 ± 14.6 Treated: 80.6 ± 12.2 (+55.8%) |
| Navaho Blackberries | 1 MHz 500 W 20 hrs. | +6 days | Control: 25.9 ± 8.9 Treated: 64.8 ± 11.5 (+38.9%) |
| Navaho Blackberries | 1 MHz 500 W 20 hrs. | +14 days | Control: 1.7 ± 3.1 Treated: 21.2 ± 12.9 (+19.5%) |
| Navaho Blackberries | 1 MHz 500 W 2 hrs. | +26 days | Control: 63.0 ± 14.3 Treated: 93.8 ± 4.0 (+30.8%) |

TABLE 6

| Sample | RF Treatment | Storage | Elapsed Time (days) | Observation |
|---|---|---|---|---|
| Blackberries (Navaho) | 70 W; 86 MHz; 1 h | ~22° C. | 3 | No infection |
| Blackberries (Navaho) | 70 W; 86 MHz; 1 h | ~22° C. | 11 | No infection |
| Blackberries (Navaho) | 70 W; 86 MHz; 1 h (Repeat Experiment) | ~22° C. | 4 | No infection |
| Raspberries (Heritage) | 70 W; 86 MHz; 1 h | ~22° C. | 3 | No infection |
| Raspberries (Heritage) | 70 W; 86 MHz; 1 h (Repeat Experiment) | ~22° C. | 4 | No infection |
| Blueberries (O'Neil) | 70 W; 86 MHz; 1 h | ~22° C. | 3 | No infection |
| Blueberries (Brightwell) | 70 W; 86 MHz; 1 h (Repeat Experiment) | ~22° C. | 4 | No infection |

TABLE 7

| Frequency (MHz) | Sample (Geometry) | Sample Mass (g) | RF Input Power (W) | Process Time (min) | Max Temp. (° C.) | Observations |
|---|---|---|---|---|---|---|
| 86 | Raspberries (Petri Dish) | 40 | 70 | 60 | ~45 | RT-Microbial Control Minimal Damage |
| 86 | Raspberries (Petri Dish) | 40 | 70 | 60 | ~45 | RT-Microbial Control Minimal Damage |
| 86 | Raspberries (Petri Dish) | 40 | 70 | 360 | ~45 | RT-Microbial Control Some Damage |
| 86 | Blackberries (Petri Dish) | 44 | 70 | 60 | ~45 | RT-Microbial Control Minimal Damage |
| 86 | Blackberries (Petri Dish) | 44 | 70 | 60 | ~45 | RT-Microbial Control Minimal Damage |
| 86 | Blackberries (Petri Dish) | 44 | 70 | 360 | ~45 | RT-Microbial Control Some Damage |
| 86 | Blueberries (Petri Dish) | 45 | 70 | 60 | ~45 | RT-Microbial Control Minimal Damage |
| 86 | Blueberries (Petri Dish) | 45 | 70 | 60 | ~45 | RT-Microbial Control Minimal Damage |
| 86 | Blueberries (Petri Dish) | 45 | 70 | 360 | ~45 | RT-Microbial Control Some Damage |

TABLE 8

| Frequency (MHz) | RF Input Power (W) | RF Field Intensity (V/cm) | Process Time (min) | Max Temp. (° C.) | Observations |
|---|---|---|---|---|---|
| 116 | 500 | 70.2 | 1.25 | 40 | RS-Microbial Control Extensive Damage |
| 116 | 100 | 31.3 | 9.7 | 40 | RS-Microbial Control Minimal Damage |
| 116 | 40 | 19.9 | 21.7 | 40 | RS-Microbial Control No Damage |
| 116 | 40 | 19.9 | 24 | 50 | RS-Microbial Control Some Location Damage |
| 116 | 20 | 14.0 | 37.5 | 40 | RS-Microbial Control No Damage |
| 116 | 12 | 9.9 | 57.8 | 40 | RS-Microbial Control No Damage |

What is claimed is:

1. A method for treating a product wherein said product potentially comprises one or more infective organisms, said method comprising:

introducing a radio frequency field to a product comprising a host material;

wherein said radio frequency field is configured to resonantly introduce thermal energy to said host material at a frequency;

wherein said product responds to said radio frequency field as a resonant cavity at said frequency;

wherein said radio frequency field is configured at a power such that said thermal energy causes only reversible changes in said host material; and wherein said thermal energy is sufficient to cause irreversible changes in said infective organisms.

2. A method as recited in claim 1, wherein said host material exhibits inherent metabolic or physiologic activity; and wherein said reversible changes preserve said host material's inherent metabolic or physiologic activity.

3. A method as recited in claim 2, wherein said host material comprises fresh fruit; and wherein said thermal energy is sufficient to achieve a temperature between 30° C. and 60° C. in said host material.

4. A method as recited in claim 2, wherein said host material comprises fresh vegetables; and wherein said thermal energy is sufficient to achieve a temperature between 30° C. and 60° C. in said host material.

5. A method as recited in claim 2, wherein said host material comprises dry foods; and wherein said thermal energy is sufficient to achieve a temperature between 30° C. and 90° C. in said host material.

6. A method as recited in claim 2, wherein said host material comprises processed foods; and wherein said thermal energy is sufficient to achieve a temperature between 30° C. and 90° C. in said host material.

7. A method as recited in claim 2, wherein said host material comprises raw high-protein foods; and wherein said thermal energy is sufficient to achieve a temperature between 30° C. and 75° C. in said host material.

8. A method as recited in claim 2, wherein said host material comprises dairy products; and wherein said thermal energy is sufficient to achieve a temperature between 30° C. and 70° C. in said host material.

9. A method as recited in claim 2, wherein said host material comprises food additives; and wherein said thermal energy is sufficient to achieve a temperature between 30° C. and 90° C. in said host material.

10. A method as recited in claim 2, wherein said host material comprises wood; and wherein said thermal energy is sufficient to achieve a temperature between 30° C. and 90° C. in said host material.

11. A method as recited in claim 2, wherein said host material comprises waste materials; and wherein said thermal energy is sufficient to achieve a temperature between 30° C. and 90° C. in said host material.

12. A method as recited in claim 2, wherein said host material comprises soil; and wherein said thermal energy is sufficient to achieve a temperature between 20° C. and 80° C. in said host material.

13. A method as recited in claim 2, wherein said host material comprises soil amendments; and wherein said thermal energy is sufficient to achieve a temperature between 20° C. and 80° C. in said host material.

14. A method as recited in claim 2, wherein said host material comprises plants; and wherein said thermal energy is sufficient to achieve a temperature between 30° C. and 60° C. in said host material.

15. A method as recited in claim 2, wherein said host material comprises plant seeds; and wherein said thermal energy is sufficient to achieve a temperature between 30° C. and 75° C. in said host material.

16. A method as recited in claim 1, wherein said host material exhibits sensory or storage properties associated with a chemical or molecular structure; and wherein said reversible changes preserve said host material's chemical or molecular structure.

17. A method as recited in claim 16, wherein said host material comprises an artifact; and wherein said thermal energy is sufficient to achieve a temperature between 30° C. and 90° C. in said host material.

18. A method as recited in claim 17, wherein said host material comprises wood-derived materials.

19. A method as recited in claim 17, wherein said host material comprises organic fibers.

20. A method as recited in claim 17, wherein said host material comprises synthetic fabrics.

21. A method as recited in claim 17, wherein said host material comprises man-made ceramics.

22. A method as recited in claim 17, wherein said host material comprises organic-based paints.

23. A method as recited in claim 17, wherein said host material comprises water-based paints.

24. A method as recited in claim 1:

wherein said host material exhibits inherent metabolic or physiologic activity;

wherein said reversible changes preserve said host material's inherent metabolic or physiologic activity; and wherein said irreversible changes decrease the infective organism's ability to reproduce or decrease the infective organism's ability to live.

25. A method as recited in claim 24:

wherein said host material comprises fresh fruit; and wherein said thermal energy is sufficient to achieve a temperature between 30° C. and 60° C. in said host material.

26. A method as recited in claim 24:

wherein said host material comprises fresh vegetables; and wherein said thermal energy is sufficient to achieve a temperature between 30° C. and 60° C. in said host material.

27. A method as recited in claim 24:

wherein said host material comprises dry foods; and wherein said thermal energy is sufficient to achieve a temperature between 30° C. and 90° C. in said host material.

28. A method as recited in claim 24:

wherein said host material comprises processed foods; and wherein said thermal energy is sufficient to achieve a temperature between 30° C. and 90° C. in said host material.

29. A method as recited in claim 24:

wherein said host material comprises raw high-protein foods; and wherein said thermal energy is sufficient to achieve a temperature between 30° C. and 75° C. in said host material.

30. A method as recited in claim 24:

wherein said host material comprises dairy products; and wherein said thermal energy is sufficient to achieve a temperature between 30° C. and 70° C. in said host material.

31. A method as recited in claim 24:

wherein said host material comprises food additives; and wherein said thermal energy is sufficient to achieve a temperature between 30° C. and 90° C. in said host material.

32. A method as recited in claim 24:

wherein said host material comprises wood; and wherein said thermal energy is sufficient to achieve a temperature between 30° C. and 90° C. in said host material.

33. A method as recited in claim 24:

wherein said host material comprises waste materials; and wherein said thermal energy is sufficient to achieve a temperature between 30° C. and 90° C. in said host material.

34. A method as recited in claim 24:

wherein said host material comprises soil; and wherein said thermal energy is sufficient to achieve a temperature between 20° C. and 80° C. in said host material.

35. A method as recited in claim 24:

wherein said host material comprises soil amendments; and wherein said thermal energy is sufficient to achieve a temperature between 20° C. and 80° C. in said host material.

36. A method as recited in claim 24:

wherein said host material comprises plants; and wherein said thermal energy is sufficient to achieve a temperature between 30 C. and 60° C. in said host material.

37. A method as recited in claim 24:

wherein said host material comprises plant seeds; and wherein said thermal energy is sufficient to achieve a temperature between 30° C. and 75° C. in said host material.

38. A method as recited in claim 1:

wherein said host material exhibits sensory or storage properties associated with a chemical or molecular structure;

wherein said reversible changes preserve said host material's chemical or molecular structure; and wherein said irreversible changes decrease the infective organism's ability to reproduce or decrease the infective organism's ability to live.

39. A method as recited in claim 38:

wherein said host material comprises an artifact; and wherein said thermal energy is sufficient to achieve a temperature between 30° C. and 90° C. in said host material.

40. A method as recited in claim 39, wherein said host material comprises wood-derived materials.

41. A method as recited in claim 39, wherein said host material comprises organic fibers.

42. A method as recited in claim 39, wherein said host material comprises synthetic fabrics.

43. A method as recited in claim 39, wherein said host material comprises man-made ceramics.

44. A method as recited in claim 39, wherein said host material comprises organic-based paints.

45. A method as recited in claim 39, wherein said host material comprises water-based paints.

* * * * *